US012579706B2

(12) United States Patent
Wang et al.

(10) Patent No.: US 12,579,706 B2
(45) Date of Patent: Mar. 17, 2026

(54) IMAGE GENERATION WITH FLEXIBLE SAMPLER FOR DIFFUSION MODELING

(71) Applicant: Generate Biomedicines, Inc., Somerville, MA (US)

(72) Inventors: Wujie Wang, Toronto (CA); John Ingraham, Cambridge, MA (US)

(73) Assignee: Generate Biomedicines, Inc., Somerville, MA (US)

( * ) Notice: Subject to any disclaimer, the term of this patent is extended or adjusted under 35 U.S.C. 154(b) by 50 days.

(21) Appl. No.: 18/658,845

(22) Filed: May 8, 2024

(65) Prior Publication Data

US 2024/0404123 A1     Dec. 5, 2024

Related U.S. Application Data

(60) Provisional application No. 63/578,763, filed on Aug. 25, 2023, provisional application No. 63/522,538, filed on Jun. 22, 2023, provisional application No. 63/470,672, filed on Jun. 2, 2023, provisional application No. 63/469,822, filed on May 30, 2023, provisional application No. 63/469,821, filed on May 30, 2023.

(51) Int. Cl.

| | |
|---|---|
| *G06T 11/00* | (2006.01) |
| *G06F 3/04847* | (2022.01) |
| *G06T 5/70* | (2024.01) |
| *G16B 15/20* | (2019.01) |

(52) U.S. Cl.
CPC ............... *G06T 11/00* (2013.01); *G06T 5/70* (2024.01); *G16B 15/20* (2019.02); *G06F 3/04847* (2013.01); *G06T 2200/24* (2013.01)

(58) Field of Classification Search
CPC ....... G06T 11/00; G06T 7/20; G06T 2200/24; G16B 15/20; G06F 3/04847
See application file for complete search history.

(56) References Cited

U.S. PATENT DOCUMENTS

| | | |
|---|---|---|
| 2022/0189579 A1 | 6/2022 | Si et al. |
| 2022/0270711 A1 | 8/2022 | Feala et al. |
| 2024/0161864 A1 | 5/2024 | Ingraham |

OTHER PUBLICATIONS

International Search Report and Written Opinion for International Application No. PCT/US2023/037034 mailed Mar. 5, 2024.
Invitation to Pay Additional Fees for International Application No. PCT/US2023/037034 mailed Jan. 5, 2024.

(Continued)

*Primary Examiner* — Michelle Chin
(74) *Attorney, Agent, or Firm* — Wolf, Greenfield & Sacks, P.C.

(57) ABSTRACT

A system performs image generation with a flexible sampler used in a diffusion model. The system receives a set of sampling parameter(s) to tailor sampling. The sampling parameter(s) include a combination of a momentum sampling parameter, a mass sampling parameter, a friction sampling parameter, an equilibration sampling parameter, and an inverse temperature sampling parameter. The system modifies a sampling operation based on the sampling parameter(s). The system applies a diffusion model with the modified sampling operation to generate a synthetic image. The system may present the synthetic image on a graphical user interface.

16 Claims, 9 Drawing Sheets

(56) References Cited

OTHER PUBLICATIONS

Anand et al., Generative Modeling for Protein Structures. 32nd Conference on Neural Information Processing Systems (NeurIPS 2018). 2018: 12 pages.

Anand et al., Protein sequence design with a learned potential. Nature communications. Feb. 8, 2022;13(1):746.

Anand et al., Protein Structure and Sequence Generation with Equivariant Denoising Diffusion Probabilistic Models. arXiv Preprint arXiv:2205.15019v1. May 26, 2022. 18 pages.

Barnes et al., A hierarchical O (N log N) force-calculation algorithm. nature. Dec. 4, 1986;324(6096):446-9.

Battaglia et al., Relational Inductive Biases, Deep Learning, and Graph Networks. arXiv:1806.01261 v3. Oct. 17, 2018. 40 pages.

Bittracher et al., A Weak Characterization of Slow Variables in Stochastic Dynamical Systems. arXiv:2005.01631 v1. May 4, 2020. 20 pages.

Cao et al., Design of protein-binding proteins from the target structure alone. Nature. May 19, 2022;605(7910):551-60.

Castro et al., Transformer-based protein generation with regularized latent space optimization. Nature Machine Intelligence. Oct. 2022;4(10):840-51.

Dauparas et al., Robust deep learning-based protein sequence design using ProteinMPNN. Science. Oct. 7, 2022;378(6615):49-56.

Eguchi et al., Ig-VAE: Generative modeling of protein structure by direct 3D coordinate generation. PLoS computational biology. Jun. 27, 2022;18(6):e1010271.

Ferruz et al., A deep unsupervised language model for protein design. BioRxiv. Mar. 12, 2022. 14 pages.

Gao et al., Deep learning in protein structural modeling and design. Patterns. Dec. 11, 2020;1(9). 23 pages.

Gilmer et al., Neural message passing for Quantum chemistry. Proceedings of the 34th International Conference on Machine Learning—vol. 70 Aug. 6, 2017. 10 pages.

Greener et al., Design of metalloproteins and novel protein folds using variational autoencoders. Scientific reports. Nov. 1, 2018;8(1):16189.

Huang et al., The coming of age of de novo protein design. Nature. Sep. 15, 2016;537(7620):320-7.

Ingraham et al., Generative models for graph-based protein design. Proceedings of the 33rd International Conference on Neural Information Processing Systems. 2019;32. 12 pages.

Joh et al., De novo design of a transmembrane Zn2+-transporting four-helix bundle. Science. Dec. 19, 2014;346(6216):1520-4.

Jumper et al., Highly accurate protein structure prediction with AlphaFold. nature. Aug. 2021;596(7873):583-9.

Koga et al., Principles for designing ideal protein structures. Nature. Nov. 8, 2012;491(7423):222-7.

Kries et al., De novo enzymes by computational design. Current opinion in chemical biology. Apr. 1, 2013;17(2):221-8.

Kuhlman et al., Advances in protein structure prediction and design. Nature reviews molecular cell biology. Nov. 2019;20(11):681-97.

Lee et al., ProteinSGM: Score-based generative modeling for de novo protein design. bioRxiv. Jul. 13, 2022. 20 pages.

Lin et al., Deep generative models create new and diverse protein structures. InMachine Learning for Structural Biology Workshop, NeurIPS 2021. 17 pages.

Luo et al., Antigen-Specific Antibody Design and Optimization with Diffusion-Based Generative Models. bioRxiv Preprint. Jul. 11, 2022. 13 pages.

Madani et al., ProGen: Language Modeling for Protein Generation. arXiv:2004.03497v1. Mar. 8, 2020. 17 pages.

Notin et al., Tranception: Protein Fitness Prediction with Autoregressive Transformers and Inference-time Retrieval. Proceedings of the 39th International Conference on Machine Learning. Jul. 2022. 28 pages.

Ramesh et al., Hierarchical Text-Conditional Image Generation with CLIP Latents. arXiv:2204.06125v1. Apr. 13, 2022. 27 pages.

Ramesh et al., Zero-shot text-to-image generation. Proceedings of the 37th International Conference on Machine Learning. 2020. 11 pages.

Riesselman et al., Deep Generative Models of Genetic Variation Capture the Effects of Mutations. Nat Methods. Author Manuscript: available in PMC Aug. 14, 2019. Published in final edited form as: Nat Methods. Oct. 2018;15(1):816-822.

Rives et al., Biological structure and function emerge from scaling unsupervised learning to 250 million protein sequences. Proceedings of the National Academy of Sciences. Apr. 13, 2021;118(15):e2016239118.

Saharia et al., Photorealistic text-to-image diffusion models with deep language understanding. Proceedings of the 36th International Conference on Neural Information Processing Systems. Nov. 28, 2022. 16 pages.

Smith, Natural Selection and the Concept of a Protein Space. Nature, vol. 225, No. 5232, Feb. 7, 1970, pp. 563-564.

Sohl-Dickstein et al., Deep unsupervised learning using nonequilibrium thermodynamics. Proceedings of the 32nd International Conference on International Conference on Machine Learning. Jul. 2015 6:37. 10 pages.

Song et al., Score-Based Generative Modeling through Stochastic Differential Equations. International Conference on Learning Representations. 2021. 36 pages.

Strokach et al., Deep generative modeling for protein design. Current opinion in structural biology. Feb. 1, 2022;72:226-36.

Trippe et al., Diffusion probabilistic modeling of protein backbones in 3d for the motif-scaffolding problem. arXiv:2206.04119. Jun. 8, 2022. 27 pages.

Trippe et al., Diffusion Probabilistic Modeling of Protein Backbones in 3D for the motif-scaffolding problem. The Eleventh International Conference on Learning Representations. 30 pages.

Watson et al., De novo design of protein structure and function with RFdiffusion. Nature. Aug. 31, 2023;620(7976):1089-100.

Wu et al., EBM-Fold: fully-differentiable protein folding powered by energy-based models. arXiv:2105.04771. May 31, 2021. 18 pages.

Wu et al., Protein Structure Generation via Folding Diffusion. arXiv:2209.15611v2. Nov. 24, 2022. 27 pages.

Yue et al., Inverse protein folding problem: designing polymer sequences. Proceedings of the National Academy of Sciences. May 1, 1992;89(9):4163-7.

Avery et al., Protein function analysis through machine learning. Biomolecules. Sep. 6, 2022;12(9):1246. 50 pages.

Kayser et al. (eds), Pharmaceutical biotechnology: drug discovery and clinical applications. Second, Completely Revised and Greatly Enlarged Edition. John Wiley & Sons. May 21, 2012. 658 pages.

International Search Report and Written Opinion for International Application No. PCT/US2024/028426 mailed Aug. 22, 2024.

Corso, Modeling Molecular Structures with Intrinsic Diffusion Models. arXiv preprint arXiv:2302.12255. Feb. 23, 2023. 6 pages.

Gong et al., Diffuseq: Sequence to sequence text generation with diffusion models. arXiv preprint arXiv:2210.08933. Feb. 14, 2023. 20 pages.

Ingraham et al., Illuminating protein space with a programmable generative model. bioRxiv. Dec. 2, 2022. 42 pages.

Zhang et al., Cross-Modal Contrastive Learning for Text-to-Image Generation. arXiv preprint arXiv:2101.04702. Apr. 14, 2022. 19 pages.

Zhang et al., Text-to-image diffusion models in generative AI: A survey. arXiv preprint arXiv:2303.07909. Apr. 2, 2023. 13 pages.

First Sampled State 314

Intermediate Sampled States 316

Final Sampled State 318

Sampling Parameters 312

Sampling Module 110

Energy Function 300

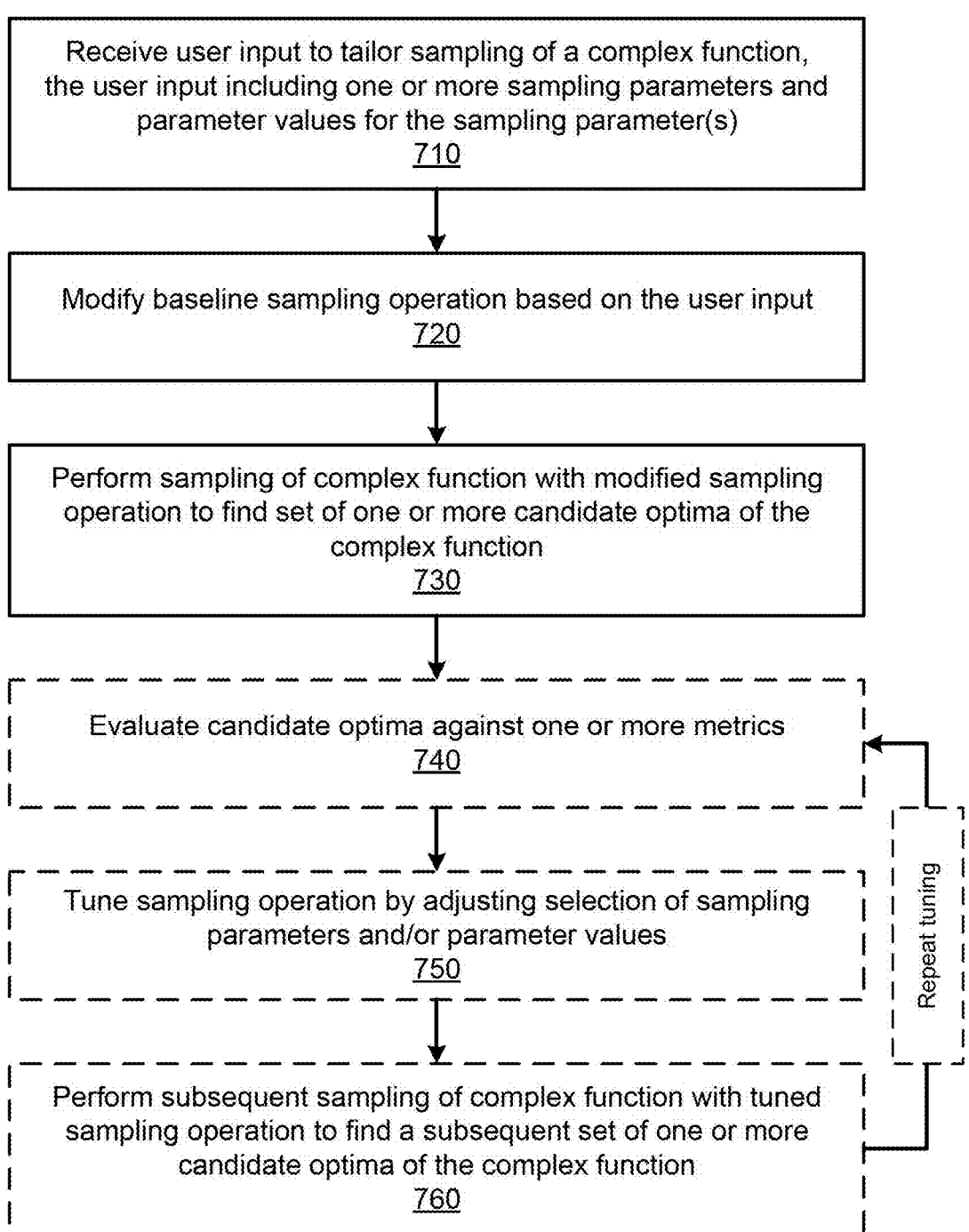

Sampling
700

Receive user input to tailor sampling of a complex function, the user input including one or more sampling parameters and parameter values for the sampling parameter(s)
710

Modify baseline sampling operation based on the user input
720

Perform sampling of complex function with modified sampling operation to find set of one or more candidate optima of the complex function
730

Evaluate candidate optima against one or more metrics
740

Tune sampling operation by adjusting selection of sampling parameters and/or parameter values
750

Perform subsequent sampling of complex function with tuned sampling operation to find a subsequent set of one or more candidate optima of the complex function
760

Repeat tuning

FIG. 7

Diffusion Model Training
800

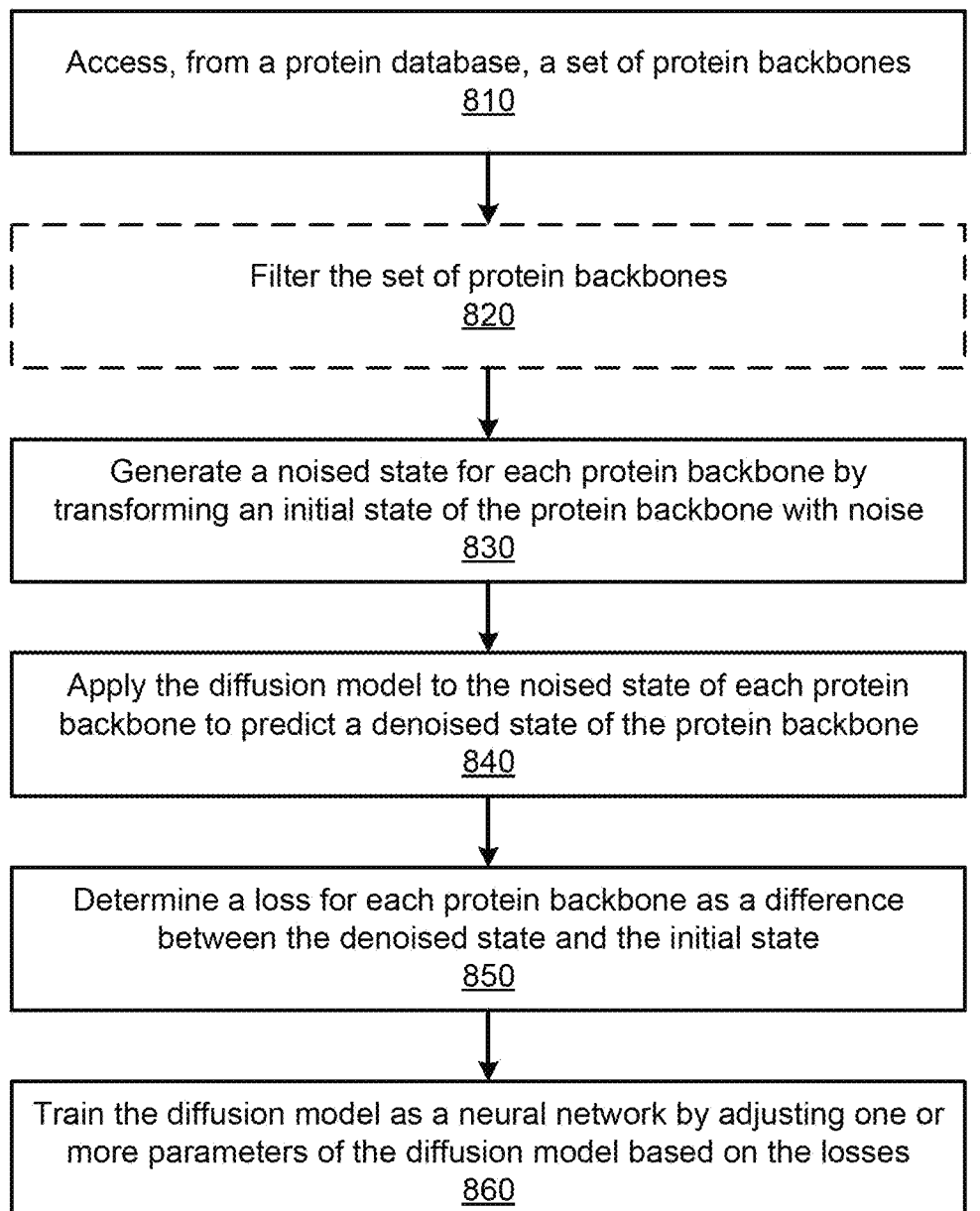

Access, from a protein database, a set of protein backbones
810

Filter the set of protein backbones
820

Generate a noised state for each protein backbone by transforming an initial state of the protein backbone with noise
830

Apply the diffusion model to the noised state of each protein backbone to predict a denoised state of the protein backbone
840

Determine a loss for each protein backbone as a difference between the denoised state and the initial state
850

Train the diffusion model as a neural network by adjusting one or more parameters of the diffusion model based on the losses
860

FIG. 8

Protein Generation
900

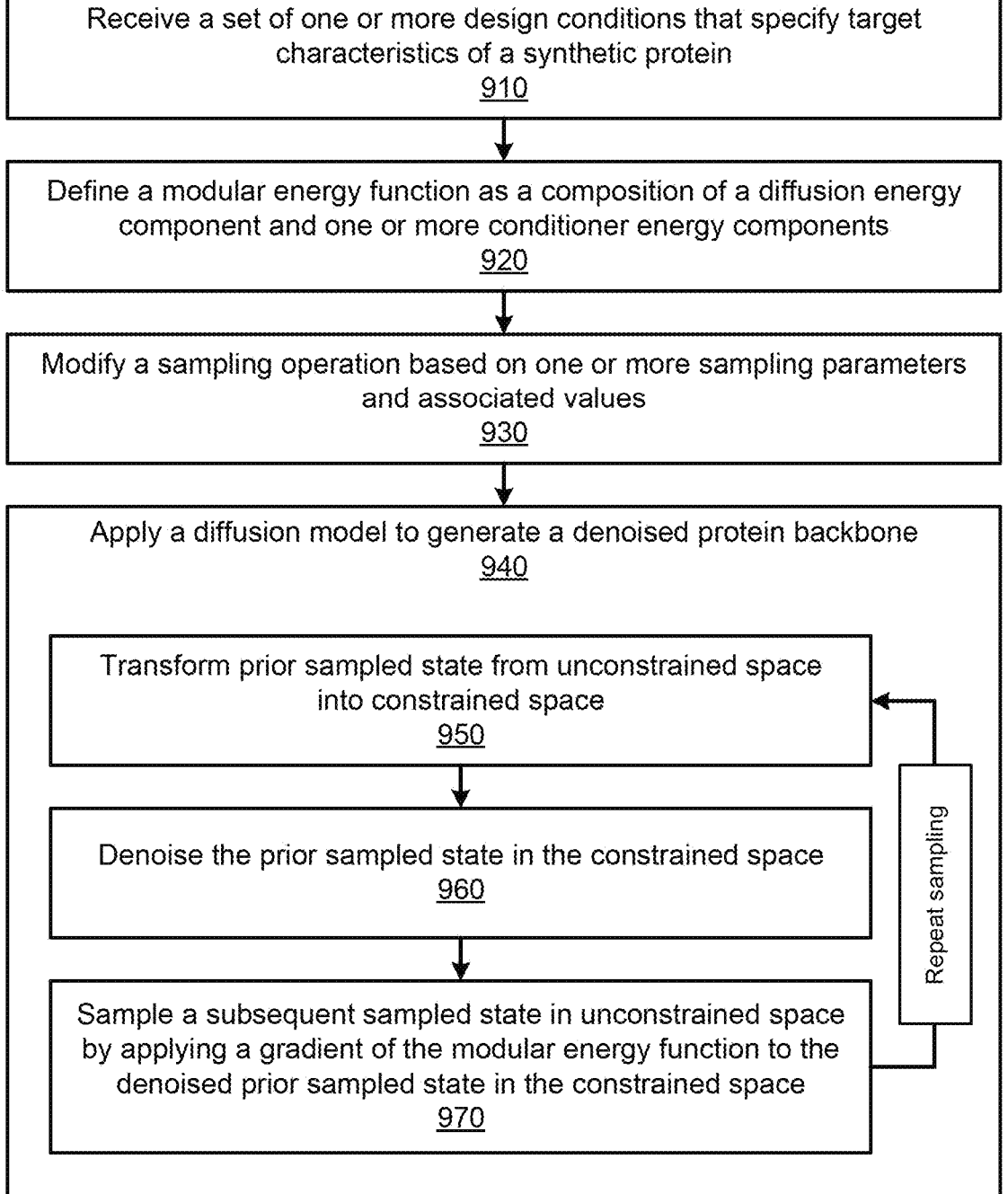

Receive a set of one or more design conditions that specify target
characteristics of a synthetic protein
910

Define a modular energy function as a composition of a diffusion energy
component and one or more conditioner energy components
920

Modify a sampling operation based on one or more sampling parameters
and associated values
930

Apply a diffusion model to generate a denoised protein backbone
940

Transform prior sampled state from unconstrained space
into constrained space
950

Denoise the prior sampled state in the constrained space
960

Sample a subsequent sampled state in unconstrained space
by applying a gradient of the modular energy function to the
denoised prior sampled state in the constrained space
970

Repeat sampling

FIG. 9

IMAGE GENERATION WITH FLEXIBLE SAMPLER FOR DIFFUSION MODELING

CROSS-REFERENCE TO RELATED APPLICATIONS

The present application claims the benefit of and priority to U.S. Provisional Application No. 63/469,821 filed on May 30, 2023, U.S. Provisional Application No. 63/469,822 filed on May 30, 2023, U.S. Provisional Application No. 63/470, 672 filed on Jun. 2, 2023, U.S. Provisional Application No. 63/522,538 filed on Jun. 22, 2023, and U.S. Provisional Application No. 63/578,763 filed on Aug. 25, 2023, all of which are incorporated by reference in their entirety.

BACKGROUND

Generating structured data objects (e.g., image generation) with diffusion models is a difficult task. Generally, a diffusion model learns a reverse diffusion process to sample a complex, high-dimensional probabilistic distribution. Exploration of the complex, high-dimensional space is computationally costly. Further, the diffusion model may be prone to tunneling into high likelihood regions, which may yield high quality structured data objects but sacrificing diversity in structured data objects generated. In an image generation context, this may lead to the diffusion model leading to a batch of high-quality images that all look similar, underscoring the difficulty in exploring the high-dimensional space. These tradeoffs are further exacerbated by limited computational budgets in the generative process.

SUMMARY

An analytics system implements a flexible sampler for a diffusion model to generate structured data objects (e.g., images). A structured data object is a set of data in a pre-defined structure (e.g., a vector, a matrix, a spreadsheet, a graph, a database, etc.). In the context of image generation, the image is an example structured data object.

The analytics system generates a graphical user interface to interface with a user performing the data object generation (e.g., image generation). The system receives, via the graphical user interface, a set of one or more design conditions for generating the structured data object (e.g., an image). Design conditions are effectively target characteristics of the structured data object to be designed. In one or more embodiments, the analytics system generates an objective function that the flexible sampler is optimizing. The objective function defines the high-dimensional space based on the design conditions. During deployment, the diffusion model is configured to iteratively denoise from an initial random state in the space to traverse from the noised distribution to the denoised distribution, yielding the resultant structured data object. In one or more embodiments, the diffusion model may be applied to generate synthetic images from a text prompt.

The analytics system further receives, e.g., via the graphical user interface, user selection of one or more sampling parameters from the combined set of sampling parameters. The analytics system may also receive a value for each of the selected sampling parameters. The flexible sampler may leverage a combination of sampling parameters to adapt the stochastic sampling for different types of complex functions. Based on the selected sampling parameters and corresponding values, the analytics system may modify a baseline sampling operation to generate a modified sampling operation. Based on the modified sampling operation, the analytics system may perform iterative stochastic sampling in conjunction with the diffusion model to generate the target structured data object (e.g., the image). In one or more embodiments, the graphical user interface may render sampled states of the structured data object (e.g., the image) during the reverse diffusion sampling process.

The graphical user interface providing the options for a user to provide input to adapt the flexible sampler provides for an improvement to computer functionality. With the variable inputs, the flexible sampler can be adapted to guide the generative process. If, for one generative workflow, high quality structured data objects is desired, the flexible sampler can bias the generative process towards the high-likelihood regions yielding the high quality results. If, however, for another generative workflow, diversity is desired, the flexible sampler can, alternatively, bias the generative process towards diversity in results. Such flexibility is particularly helpful when the computation budget is limited.

BRIEF DESCRIPTION OF THE DRAWINGS

FIG. 7 is a method flowchart of sampling with a flexible sampling operation, according to one or more embodiments.

FIG. 8 is a method flowchart of training a diffusion model for de novo protein design, according to one or more embodiments.

FIG. 9 is a method flowchart of deploying a diffusion model for de novo protein design leveraging the flexible sampling operation, according to one or more embodiments.

Figure 1:
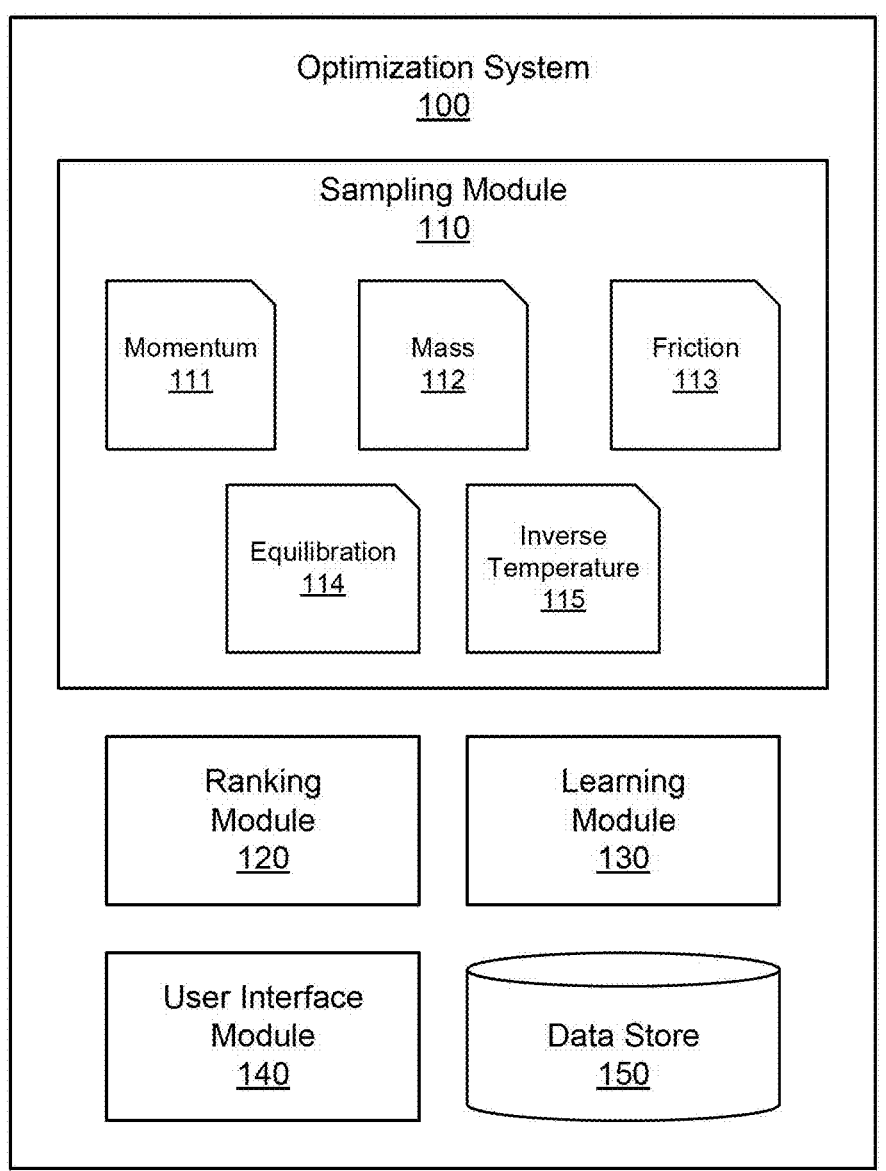
FIG. 1 is a block diagram of an optimization system implementing a flexible sampling operation to optimize a complex function, according to one or more embodiments.

The figures are illustrative, describing principles in one or more embodiments. They are meant to be representative, thus not limiting the scope of the principles to what's illustrated. The following description provides further detail relating to the principles illustrated and represented in the figures.

DETAILED DESCRIPTION

Overview

One of the cornerstone technical challenges in optimizing complex functions is intelligently traversing complex, unknown spaces. For example, a steepest descent algorithm may, at each sampling step, seek to identify the steepest descending direction to perform subsequent sampling of the complex function. Such approach forgets all past sampling steps beyond the present sampling step. Thus, in certain instances, the steepest descent algorithm may take inefficient sampling approaches that fail to account for momentum of the entire sampling process. In other instances, sampling algorithms make take uniformly-sized steps that may over-step high likelihood regions, missing the opportunity to hone in to unexpecting optima in those regions. In yet other instances, sampling algorithms tunnel into local optima and lack the ability to explore beyond the local optima. To account for these pitfalls, sampling algorithms can initialize sampling at diverse start points across the function space. However, each of such start points are still susceptible to such pitfalls.

To overcome such pitfalls, a flexible sampler is implemented to adaptively sample the contours of the complex function space (e.g., complex probabilistic data distributions in diffusion model generative processes). The sampling operation leverages a combination of sampling parameters that can adapt the sampling operation to best optimize a complex function. Based on the modified sampling operation, the analytics system may perform iterative stochastic sampling to find optima of the complex function. Such sampling operation can be readily adapted to a variety of optimization problems, including resource management, image generation, de novo protein design, structured data object generation, protein structure solving, etc. A structured data object is a set of data in a pre-defined structure (e.g., a vector, a matrix, a spreadsheet, a graph, a database, etc.). For example, a structured data object may be an image represented in matrix form including pixel intensity values in one or more color channels. As another example, a structured data object may be a graph including nodes and edges. In one example of a graph, the graph may be a knowledge graph representing real-world entities (e.g., people, places, businesses) and the relations between such entities. Such novel knowledge graph can be implemented in gaming contexts to generate a simulated community. In a further example, the graph may represent a protein backbone, including heavy atoms in a peptide chain and relative positioning of the heavy atoms.

The sampling parameters include a momentum, a mass, a friction, an equilibration, an inverse temperature, or some combination thereof. The momentum accumulates history of previous Newtonian forces to better navigate the contours of the complex function. This improves upon the inefficient sampling approaches that only consider the single current sampling step. The mass couples degrees of freedom together, i.e., variables to the complex function. This enhances the mixing speed of sampling dynamics by permitting the sampling operation to focus on decoupled degrees of freedom. The friction dampens the effects of the momentum. The friction may control a refreshment rate of the momentum, such that low friction minimally affects the momentum and high friction minimizes effects of the momentum. The equilibration injects noise into the sampling process to promote exploration of the search space. The equilibration can be time-dependent, such that the amount of noise can be great at the start of sampling, while decreasing over sampling time. The inverse temperature guides the sampling towards exploitation of high-likelihood states. The inverse temperature may also be time-dependent, thereby biasing the sampling towards high likelihood regions more over time.

The training of the machine-learned models described herein (such as the diffusion models, neural networks, and other models referenced herein) include the performance of one or more non-mathematical operations or implementation of non-mathematical functions at least in part by a machine or computing system, examples of which include but are not limited to data loading operations, data storage operations, data toggling or modification operations, non-transitory computer-readable storage medium modification operations, metadata removal or data cleansing operations, data compression operations, protein structure modification operations, image modification operations, noise application operations, noise removal operations, and the like. Evaluation of a function moreover may include performing one or more operations. Accordingly, the training of the machine-learned models described herein may be based on or may involve mathematical concepts, but is not simply limited to the performance of a mathematical calculation, a mathematical operation, or an act of calculating a variable or number using mathematical methods.

Likewise, it should be noted that the training of the models describes herein cannot be practically performed in the human mind alone. The models are innately complex including vast amounts of weights and parameters associated through one or more complex functions. Training and/or deployment of such models involve so great a number of operations that it is not feasibly performable by the human mind alone, nor with the assistance of pen and paper. In such embodiments, the operations may number in the hundreds, thousands, tens of thousands, hundreds of thousands, millions, billions, or trillions. For example, in de novo protein design embodiments, the training data may include hundreds, thousands, tens of thousands, hundreds of thousands, millions, or billions of protein backbones (or derivatives thereof), each protein backbone may further include hundreds, thousands, tens of thousands, hundreds of thousands, or millions of three-dimensional coordinates of heavy atoms in the peptide sequence. Accordingly, such models are necessarily rooted in computer-technology for their implementation and use.

Optimization System

FIG. 1 is a block diagram of an optimization system 100 implementing a flexible sampling operation to optimize a complex function, according to one or more embodiments. The optimization system 100 may be a computing device. The optimization system 100 can apply the sampling operation to provide optimal solutions to the complex function. Accordingly, the optimization system 100 can provide the optimal solutions to a user, or may provide such solutions to one or more other systems to implement such solutions to solve real-world problems. In one or more embodiments, the optimization system 100 may be applied to de novo protein design to craft novel protein designs that do not replicate naturally occurring proteins. In other embodiments, the optimization system 100 may be applied in protein structure solving to determine folding structure of a polypeptide chain.

In one or more embodiments, the optimization system 100 includes a sampling module 110, a ranking module 120, a learning module 130, a user interface module 140, and a data store 150. Alternative embodiments may include more, fewer, or different components from those illustrated in FIG. 1, and the functionality of each component may be divided between the components differently from the description below. Additionally, each component may perform their respective functionalities in response to a request from a human, or automatically without human intervention.

The sampling module 110 modifies and applies a flexible sampler in an optimization process. The sampling module 110 may modify a sampling operation based on a number of sampling parameters. The sampling parameters may include a momentum 111, a mass 112, a friction 113, an equilibration 114, and an inverse temperature 115. The momentum 111 accumulates history of previous Newtonian forces to better navigate the contours of the complex function. The mass 112 couples degrees of freedom together, i.e., variables to the complex function. The friction 113 dampens the effects of the momentum 111. The friction 113 may control a refreshment rate of the momentum 111, such that low friction minimally affects the momentum 111 and high friction minimizes effects of the momentum 111. The equilibration 114 injects noise into the sampling process to promote exploration of the search space. The equilibration 114 can be time-dependent, such that the amount of noise can be great at the start of sampling, while decreasing over sampling time. The inverse temperature 115 guides the sampling towards exploitation of high-likelihood states. The inverse temperature 115 may also be time-dependent, thereby biasing the sampling towards high likelihood regions more over time. The sampling module 110 modifies the sampling operation based on a combination of the above sampling parameters. For example, the sampling module 110 may modify the sampling operation according to the momentum and the friction. In another example, the sampling 110 may modify the sampling operation according to the equilibration and the mass. In other examples, the sampling operation can be modified according to any combination of sampling parameters. Such combinability provides flexibility in adapting the sampling operation to each complex function optimized for.

In one or more embodiments, the optimization system 100 is applied to sampling for a diffusion probabilistic model. In a diffusion model framework, the diffusion model is trained to learn a reverse noising process. The noising process generally entails taking a data distribution $p(x_0)$ and noising the data distribution $p(x_t|x_0) = \mathcal{N}(x_t|\alpha_t x_0, \sigma_t I)$, which generates the noise-perturbed sequence $\{x_t\}_{t=0}^T$ through a sequential noising process $p(x_{t+1}|x_t)$. This noise process can be modeled as a solution to a stochastic differential equation (SDE) in the form of $dx = f(x, t) + g(t)dw$ where $f$ and $g$ are drift and diffusion terms, respectively. Training of the diffusion model is to learn a parametric score model $s_\theta$ that captures the marginal score function $\nabla x_t \log p(x_t, t) = \nabla x_t \log \int p(x_t|x_0)p(x_0)dx_0$. This requires minimizing the evidence lower bound on the data distribution. Given the oracle $\nabla x_t \log p(x_t, t)$, a reverse SDE traverses the distribution backwards in time, yielding the reverse flow SDE:

$$dx = f(x, t)dt - g(t)^2 \nabla x \log p(x, t)dt + g(t)d\overline{w} \tag{1}$$

The associated Fokker-Planck equation that generates $p_t(x_t, t)$ has a simple ordinary differential equation (ODE) form, also termed the probability flow ODE:

$$dx = f_{ODE}(x, t)dt = f(x, t)dt - \frac{1}{2}g(t)^2 \nabla x \log p(x, t)dt \tag{2}$$

In one or more embodiments, $\nabla x \log p(x, t)$ is modeled with a parametric model. Under affine transformation, the score regression can be transformed to the noise or velocity regression problem. Learning the noise-conditioned score is akin to maximum likelihood learning.

The reverse time SDE can be rewritten to be:

$$dx = f(x, t)dt - g(t)^2 \nabla x \log p(x, t)dt + g(t)d\overline{w} = \tag{3}$$
$$\left[f(x, t)dt - \frac{1}{2}g(t)^2 \nabla x \log p(x, t)dt\right] + \left[-\frac{1}{2}g(t)^2 \nabla x \log p(x, t)dt + g(t)d\overline{w}\right]$$

The first component is the probability flow ODE, whereas the second component relates to annealed Langevin dynamics. The probability flow ODE deterministically interpolates between marginal distribution $p_t(x_t)$ at different noise levels, and the annealed Langevin Dynamics seeks to generate samples from $p_t(x_t)$ via Markov Chain Monte Carlo (MCMC) procedures. By moving from a highly noised data distribution that covers the un-noised data distribution, the annealed Langevin Dynamics facilitates mode-mixing. This idea is like simulated annealing but leverages the learned noise conditioned score function. The probability ODE reverse the non-equilibrium process, while the annealed Langevin dynamics samples the time-dependent marginals.

The flexible sampling operation for the reverse flow SDE can be express as:

$$dp = \phi(t)(-\nabla x \log p(x, t) - \gamma p)dt + \sqrt{\frac{2\gamma\phi(t)}{\lambda(t)}} M_t^{1/2}d\overline{w} \tag{4}$$
$$dx = \phi(t)M_t^{-1}pdt + f_{ODE}(x, t)dt$$

In the above equation: $\phi(t)$ is the equilibration (and can be time-dependent); M refers to the mass and aids in mode-mixing between equilibrium sampling and non-equilibrium sampling; $\gamma$ refers to the friction that dampens the momentum p; and $\lambda(t)$ is inverse temperature. Equation 4 mixes probability flow ODE with a second-order Langevin equation, which is similar to Hamiltonian Monte Carlo, with a stochastic thermostat. Other thermostat approaches may be implemented. The sampling operation can be adapted to exclude one or more of the above sampling parameters, yielding a modified sampling operation. In other embodiments, the parameter values for the sampling parameters also affect the sampling.

In one or more embodiments, the mass and its time dependence can be expressed as:

$$M_t = \frac{1}{g(t)^2}RR^T, \quad M_t^{1/2} = \frac{1}{g(t)}(R^T)^{-1} \tag{5}$$

where $RR^T$ is the covariance of the data distribution.

Sampling is influenced by the combination of sampling parameters incorporated into the sampling operation. For example, assuming unlimited equilibration and flawless parameterization of the score function $\nabla \log p(x, t)$, the sampling operation is capable of accurately sampling $p(x, t)$, akin to Equation 3. Introducing a bias, in the form of a conditioner $\log p(y|x)$ alters the underlying landscape of the probability distribution, making it challenging to sample using a standard reverse SDE approach. Accordingly, the flexible sampling operation provides adaptability:

$$dp = \phi(t)(-\nabla x \log p(x, t) - \nabla x \log p(y|x, t) - \gamma p)dt + \sqrt{\frac{2\gamma\phi(t)}{\lambda(t)}} \, M_t^{1/2} d\overline{w} \quad (6)$$

$$dx = \phi(t)M_t^{-1} p \, dt + f_{ODE}(x, t)dt$$

where the modified probability distribution is incorporated to modify the reverse SDE. These sampling parameters provide control over sampling of the modified landscape. In one or more embodiments, the modified landscape may be conditioned energy function for de novo protein design.

In other embodiments, the friction can be toggled to control effects of the momentum. For example, as the friction approaches infinity with sufficient equilibration at each noise level, the momentum ceases to effect the sampling:

$$\lim_{\gamma \to \infty} \frac{1}{\gamma} dp = \lim_{\gamma \to \infty} \frac{1}{\gamma} \phi(t) \left( -\frac{1}{\gamma} \nabla x \log p(x, t) - p \right) dt + \sqrt{\frac{2\phi(t)}{\gamma\lambda(t)}} \, M_t^{1/2} d\overline{w} = 0 \quad (7)$$

$$\phi(t)M_t^{-1} p \, dt = -M_t^{-1} \frac{\phi(t)}{\gamma} \nabla x \log p(x, t) dt + \sqrt{\frac{2\phi(t)}{\gamma\lambda(t)}} \, M_t^{-1/2} d\overline{w}$$

By setting the equilibration such that $$\frac{\phi(t)}{\gamma} = \frac{1}{2},$$

the reverse diffusion solution in Equation 3 is recovered with $\lambda(t)=1$ and $M=\mathbb{1}$ (identity matrix):

$$dx = f_{ODE}(x, t)dt - M_t^{-1} \frac{1}{2} \nabla x \log p(x, t) + M_t^{-1/2} d\overline{w} = \quad (8)$$

$$f_{ODE}(x, t)dt - g(t)^2 RR^T \frac{1}{2} \nabla x \log p(x, t) + g(t) Rd\overline{w} =$$

$$f_{ODE}(x, t)dt - g(t)^2 \frac{1}{2} \nabla x \log p(x, t) + g(t) d\overline{w}$$

In the zero-friction case, the sampler reduces to the hybrid sampler that mixes ODE and HMC sampling:

$$dp = -\phi(t)\nabla x \log p(x, t)dt \quad (9)$$

$$dx = \phi(t)M_t^{-1} p \, dt + f_{ODE}(x, t)dt$$

The sampling module 110 is configured to perform sampling with the modified sampling operation. The sampling module 110 iteratively explores the complex function space, e.g., sampling from the probability distribution, in a plurality of sampling steps. The sampling operation guides how the next sampling step is taken. In a first sampling step, the sampling module 110 may initialize a candidate solution (e.g., a random solution in the function space). The sampling module 110 inputs the solution into the complex function, yielding an output based on the input. The sampling module 110 evaluates the candidate solution based on this output. For example, the output may be a single value, which itself may be a score. Or, in other examples, the output (e.g., a vector, a matrix, or a graph) is evaluated against another objective function that scores the output. In a second sampling step, the sampling module 110 may sample a second candidate solution based on the evaluated first candidate solution and according to the sampling operation. The sampling module 110 iteratively performs the sampling steps till a stop condition is met, e.g., a number of sampling steps, marginal change or improvement in output, etc.

In one or more embodiments, the sampling module 110 may perform multiple sampling processes in parallel. When performed in parallel, the sampling module 110 initializes a starting state for each sampling process. Sampling processes may also have different sampling operations. The sampling module 110 may perform each sampling process independently of one another. In other embodiments, the sampling module 110 may share information between the sampling processes. In such embodiments, exploration of the search space for one sampling process can inform sampling of another sampling process. In one example, the momentum of one sampling process can be updated based on the momentum of one or more other sampling processes.

In one or more embodiments, the ranking module 120 selects one or more optimal solutions based on the sampling process. As a result of the sampling by the sampling module 110, the sampling process yields a plurality of candidate solutions with their evaluated scores. The ranking module 120 may select optimal solutions based on one or more selection criteria. For example, the ranking module 120 may select the optimal solutions with the highest scores. In other embodiments, the ranking module 120 may select one or more optimal solutions with the highest score, while also maximizing for diversity in solutions. This could help to providing similar or potentially redundant solutions. In other embodiments, the ranking module 120 may select the optimal solutions as the best candidate solution from sampling processes operated in parallel. For example, one sampling process may be performed using a first modified sampling operation modified according to a first permutation of sampling parameters and parameter values, whereas a second sampling process may be performed using a second modified sampling operation modified according to a second permutation of sampling parameters and parameter values. Each sampling process may yield its own set of candidate solutions. The ranking module 120 may select from the aggregate set, or individually from each set.

In one or more embodiments, the learning module 130 may tune the sampling parameters of the modified sampling operation to optimize the sampling process. The learning module 130 assesses the one or more sampling processes and their candidate solutions. The learning module 130 may identify certain sampling processes that yielded better solutions, or converged more quickly to high likelihood regions. To tune the function, the learning module 130 may adjust one or more of the sampling parameters to optimize the sampling operation for the particular optimization problem. Once tuned, the sampling module 110 may perform one or more subsequent sampling processes with the tuned function. In one or more embodiments, the learning module 130 may further tune the sampling operation during a sampling process. Based on the prior sampling steps up to a current sampling step, the learning module 130 may assess the efficiency of the sampling operation. For example, if the sampling operation is oscillating between opposite slopes of a valley in the high-dimensional space, the learning module 130 may negatively assess the efficiency of the sampling operation. In such scenario, the learning module 130 may tune the sampling operation between sampling steps, e.g., to increase the momentum, or to decrease the friction. Or, in another example, the learning module 130 may determine that the sampling operation has entered a high-likelihood region, such that the learning module 130 may increase the inverse temperature to exploit the region.

In one or more embodiments, the learning module 130 may implement a machine-learning algorithm in tuning the sampling operation. The machine-learning algorithm could collate empirical data from previously performed sampling processes. The learning module 130 may leverage the empirical data to learn patterns in how the sampling parameters affect the sample processes for a particular optimization problem. Based on the learned patterns, the learning module 130 may set and/or tune the sampling parameters for the sampling operation.

In one or more embodiments, the user interface module 140 generates a user interface for presenting content to a user of the optimization system 100 and/or receiving inputs from the user. The user interface may be a graphical user interface providing and/or receiving visual data. In such embodiments, the optimization system 100 may include hardware for presenting the user interface (e.g., an electronic display, a touch screen, a projector, a headset, etc.). The optimization system 100 may, alternatively, be in communication, wired or wirelessly, with a client computing device (not illustrated). The optimization system 100 may generate and provide the generated user interface for presentation by the client computing device.

In one or more embodiments, the user interface module 140 generates the user interface with one or more user-interactable elements for providing a user input to modify the sampling operation. For example, the user interactable elements may include virtual buttons corresponding to the available sampling parameters that may be selected from. For example, a first virtual button corresponds to the momentum sampling parameter, a second virtual button corresponds to the mass, and so on. In another example, the user interactable elements may include an input field. In yet other examples, the user interactable elements may include a slider per sampling parameter. A position of the slider along the continuum corresponds to a different number in a range of permissible values for the sampling parameter.

In one or more embodiments, the user interface module 140 generates the user interface to include a suggested ranges for each of one or more sampling parameters. The learning module 130 may provide learned ranges where the sampling operation operates optimally. Accordingly, the user interface module 140 may provide a visual indication of the suggested range. For example, the visual indication may color part of the continuum for a sampling parameter green. In some embodiments, as a user sets one sampling parameter, the suggested ranges may for other sampling parameters may update based on the set parameter value for that sampling parameter. The user interface module 140 provides the user input with the selected permutation of sampling parameters and/or parameter values to the sampling module 110 for modification of the sampling operation.

In one or more embodiments, the user interface module 140 may visualize the sampling process(es) being performed by the sampling module 110. In one or more applications, the candidate solutions may be visualized. For example, in the image generation context, the user interface may visualize the sampled states of the image throughout the reverse diffusion process. In another example, in the context of de novo protein design, each candidate solution may be a protein backbone along a denoising reverse time continuum.

Accordingly, each protein backbone may be visualized with a protein folding algorithm (i.e., one that solves the structure to determine relative position of heavy atoms in the chain). The user interface module 140 may render the folded structure of each candidate protein backbone into an image as a visual representation of the folded structure, e.g., as the sampling process is being performed. In a related example, in the context of image generation via diffusion model, each candidate solution may be a noised image along a denoising reverse time continuum. Here, the noised image can be presented in the user interface, providing a real-time visualization of the sampling process being performed according to the modified sampling operation. This provides a user with the ability to further tailor the sampling operation from the real-time visualization as feedback to the sampling process.

The data store 150 stores data used by the optimization system 100. In one or more embodiments, the data store 150 may store historical sampling processes performed by the sampling module 110. Data included under each historical sampling process may include the permutation of sampling parameters and/or parameter values used to modify the sampling operation, candidate solutions identified through the sampling process, evaluations for those candidate solutions, selected optimal solutions, or some combination thereof. The data store 150 may categorize the sampling processes into each of the various optimization problems. The data store 150 may further store the insights into how to optimize the sampling operation learned by the learning module 130 from the empirical data.

Image Generation Via Diffusion Model

Figure 2:
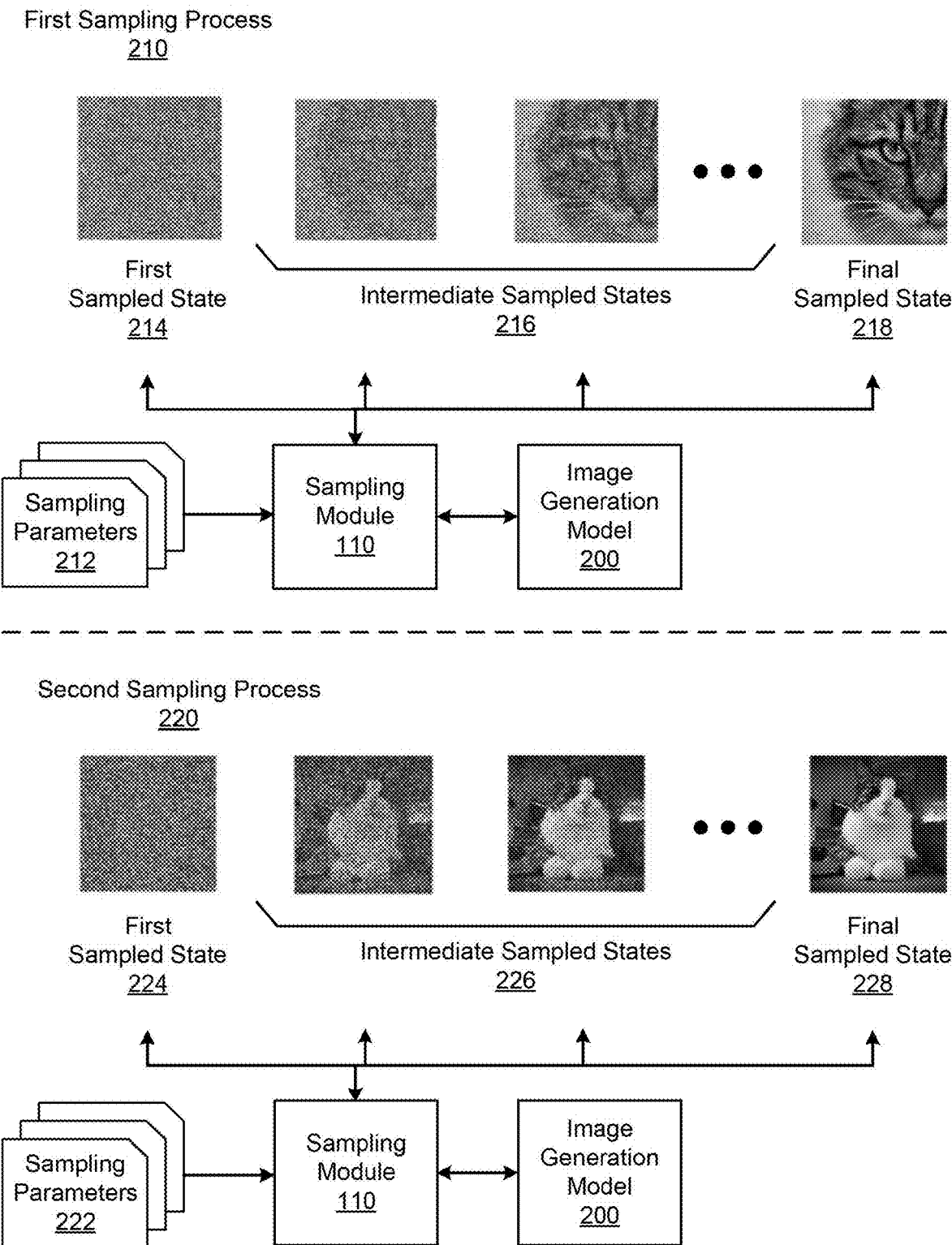
FIG. 2 illustrates the flexible sampling operation in image generation via a diffusion model, according to one or more embodiments.

FIG. 2 illustrates the flexible sampling operation in image generation via an image generation model 200, according to one or more embodiments. This illustrative image generation process may be performed by the optimization system 100 of FIG. 1. In other embodiments, some or all steps described are performed by another computing system or device.

The image generation model 200 may be a machine-learning model trained to generate images from input text prompt. The image generation model 200 transforms the text prompt into embeddings in a latent space. The image generation model 200 may employ a diffusion model that learns a reverse diffusion process that denoises random noise into synthetic images, guided further by the embeddings derived from the text prompt. The image generation model 200 may be implemented as a neural network. The neural network is trained on a dataset of real images that are injected with noise. The training process teaches the neural network how to denoise the noised images to recover the original training data. Once the neural network is trained, it can be used to generate realistic images, guided by the input text prompt. In some embodiments, the image generation model 200 may further leverage a natural language processing machine-learning model to decode the text prompt.

Here, there are two sampling processes shown: a first sampling process 210 and a second sampling process 220. Both sampling processes may have the same objective or target object to generate an image of, e.g., a cat. The first sampling process 210 is performed by the sampling module 120 using a modified sampling operation based on a first set of sampling parameters 212 and its associated parameter values. The second sampling process 220 is performed by the sampling module 120 using a modified sampling operation based on a second set of sampling parameters 222 and its associated parameter values. The first set of sampling parameters 212 is different than the second set of sampling parameters 222.

In one or more embodiments, the sampling module 110 may perform the two sampling processes in parallel. Computationally, the two processes can be performed on different processing units contemporaneously, or the same processing unit(s) at different times. In effect, the two sampling processes do not share information about the sampled probability distributions in each sampling process. Accordingly, the sampling module 110 initializes a random state as the first sampled state 214, the random state may be random noise in the image space. In the next sampling step, the sampling module 110 identifies a second sampled state based on the first sampled state 214 as applied to the modified sampling operation based on the first set of sampling parameters 212 and its associated parameter values. The sampling module 110 may iteratively sample, yielding one or more intermediate sampled states 216, until the sampling arrives at a final sampled state 218. The final sampled state 218, in the context of image generation, is a virtual image (e.g., of a cat as the target object). The second sampling process 220 also initializes a first sampled state 224, then in iterative sampling steps samples the reverse flow probability distributions to yield intermediate sampled states 226, and finally arriving at the final sampled state 228—all such sampling guided by the modified sampling operation based on the second set of parameters 222 and their corresponding values. The two sampling processes yields different results, as each sampling operation traverses the image space differently.

In one or more other embodiments, the sampling module 110 may perform the two sampling processes in series. The first sampling process 210 is first performed, yielding the final sampled state 218. Subsequently, in one or more embodiments, a user may modify the sampling parameters to arrive at the second set of sampling parameters 222 and their corresponding values to remodify the sampling operation. In other embodiments, the learning module 130 may tune the sampling parameters based on insights learned through the first sampling process 210. For example, the learning module 130 may modify the mass sampling parameter to couple or decouple certain degrees of freedom together. In one example, the mass may result in coupling color of adjacent pixels of an object in an image generation context. In another example with de novo protein design, positions of heavy atoms in the protein backbone could be coupled together.

Protein Structure Solving

Figure 3:
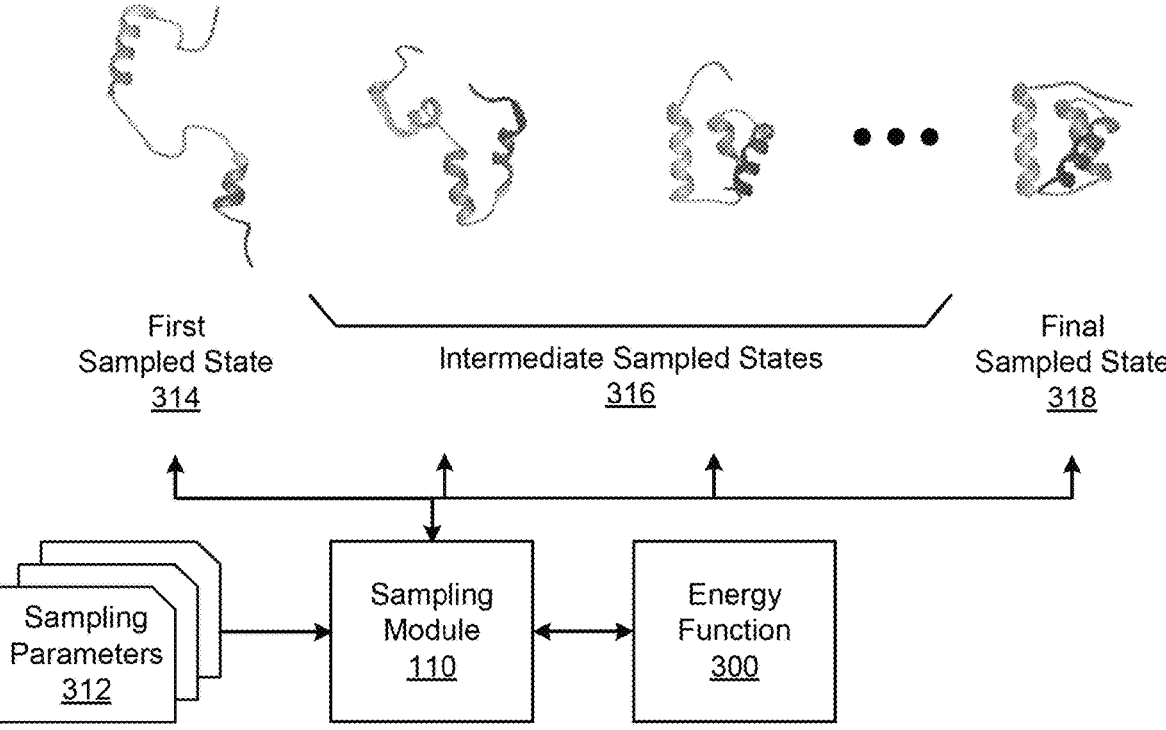
FIG. 3 illustrates the flexible sampling operation in protein structure solving, according to one or more embodiments.

FIG. 3 illustrates the flexible sampling operation in protein structure solving, according to one or more embodiments. This illustrative protein structure solving process may be performed by the optimization system 100 of FIG. 1. In other embodiments, some or all steps described are performed by another computing system or device.

Here, the optimization system 100 is aiming to determine a folding structure or configuration of a polypeptide chain. The folding is affected by molecular forces defined in an energy function 300. Accordingly, protein folding would trend towards a low energy state, where the molecular forces are in equilibrium. The sampling module 110 samples the energy landscape (i.e., defined by the energy function 300) to determine the optimal folding structure. The sampling module 110 may traverse this energy landscape according to the modified sampling operation determined based on the set of sampling parameters 312 and its associated values. The sampling module 110 may initialize a first sampled state 314, i.e., a random folding structure. In subsequent sampling steps, the sampling module 110 applies the modified sampling operation to the previous sampled state(s) to sample the next state, yielding the intermediate sampled states 316, and finally arriving at the final sampled state 318 at the last sampling step of the sampling process. Akin to image generation, the learning module 130 may learn trends or patterns from the sampling process and may tune the sampling operation to better traverse the energy landscape. For example, the learning module 130 may decrease the inverse temperature and/or increase the equilibration to further explore the energy landscape, rather than tunneling into one high-likelihood region, e.g., where one or more local optima may exist, but not the global optimum.

System Environment—de Novo Protein Design

Figure 4:
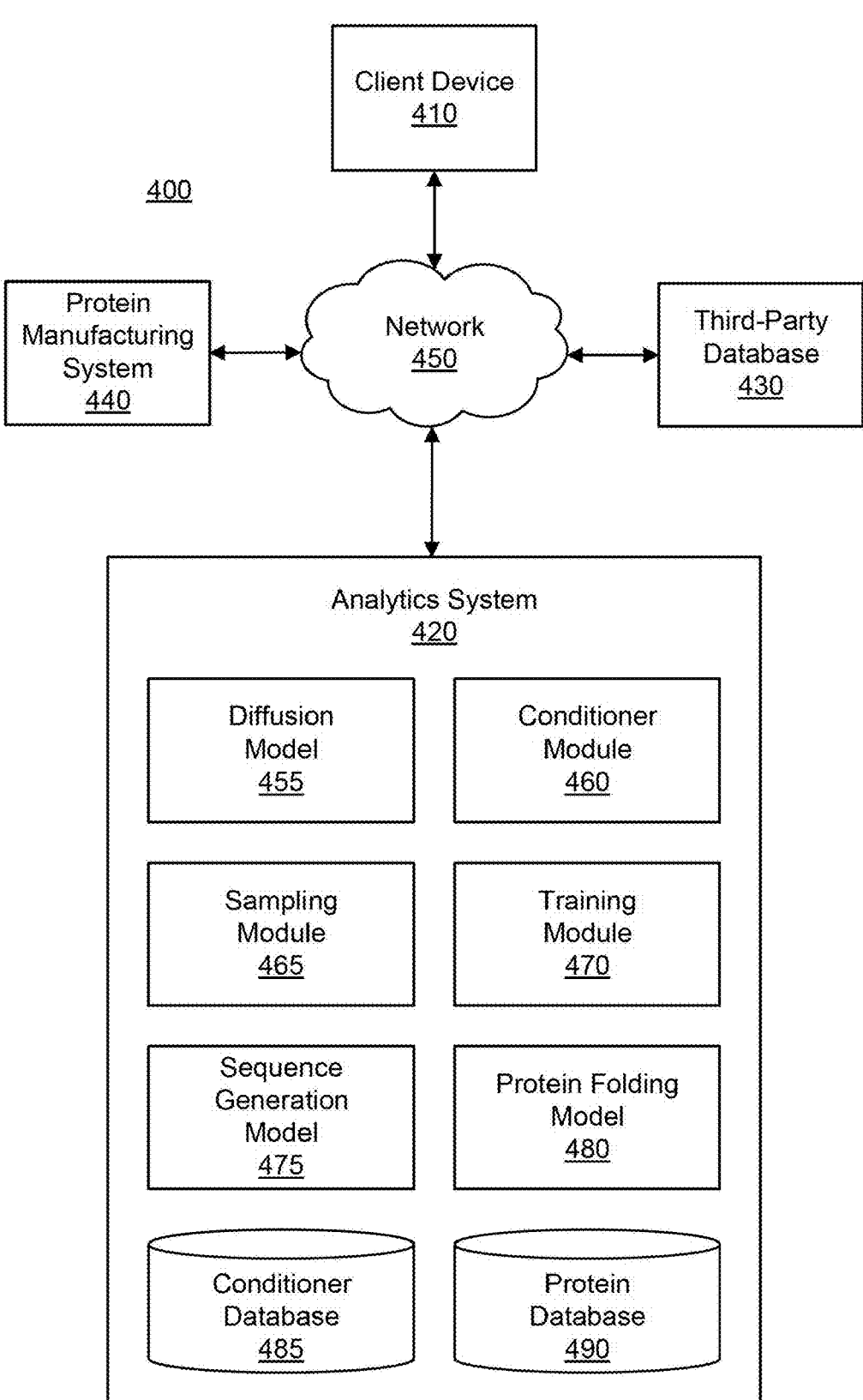
FIG. 4 is a system environment of the analytics system implementing a diffusion model for de novo protein design, according to one or more embodiments.

FIG. 4 illustrates an example system environment for an analytics system 430, in accordance with one or more embodiments. The system environment illustrated in FIG. 4A includes a client device 410, an analytics system 420, a third-party database 430, a protein manufacturing system 440, and a network 450. The analytics system 420 is an embodiment of the optimization system 100. Alternative embodiments may include more, fewer, or different components from those illustrated in FIG. 4, and the functionality of each component may be divided between the components differently from the description below. Additionally, each component may perform their respective functionalities in response to a request from a human, or automatically without human intervention.

A client device 410 may be operated by a user in designing proteins. The client device 410 is configured to receive inputs and to display results of analyses by the analytics system, including synthetic protein designs. Accordingly, the client device 410 is a computing device that interacts with other components in the system environment 400 via the network 440. In one or more embodiments, a user may provide to the client device 410 an input including a set of one or more design conditions, optionally with any other instructions, for generating one or more synthetic proteins. The client device 410 may relay the input to the analytics system 420 via the network 440 to generate the one or more synthetic proteins. After generation of the synthetic proteins, the analytics system 420 may relay the generated synthetic proteins to the client device 410 for display to the user. The user may provide additional inputs to the client device 410 to modify the generated protein designs or to regenerate protein designs.

In one or more embodiments, the client device 410 may present a design interface for protein design. The design interface may accept input in various forms. For example, the design interface may include a set of togglable menus. Each togglable menu may include target characteristics for the target protein. In one example, a first togglable menu may include all types of symmetry. Another togglable menu may include different structural motifs to include. A third togglable menu may include various protein types (e.g., antibodies, contractile proteins, enzymes, hormonal proteins, structural proteins, storage proteins, and transport proteins). Other types of input options in the design interface may include range inputs, text input, sequence input, picture input, etc. For example, the design interface may include a single text input for inputting a text string.

The analytics system 420 performs one or more computational analyses. The analytics system 420 is configured to receive inputs from the client device 410 to guide protein design. The analytics system 420 generally applies a diffusion model in conjunction with a sampling algorithm to generate a de novo protein design. The de novo protein design may be provided to a manufacturing system for manufacturing of the protein. The analytics system 420 may also provide the de novo protein design to the client device 410, e.g., for display in the design interface. The client device 410 may provide further inputs for modification of the protein design.

In one or more embodiments, the analytics system 420 generates protein design with a set of one or more design conditions that constrain the protein design. The inputs from the client device 410 may include the set of one or more design conditions including target characteristics of a protein to be generated. The analytics system 420 utilizes the design conditions to constrain application of the diffusion model. The analytics system defines a modular energy function based on the one or more design conditions. The analytics system also transforms coordinates of the sampled state from unconstrained space into constrained space based on the one or more design conditions. The analytics system traverses the protein space from an initial sampled state. At each sampling step, the analytics system utilizes the diffusion model to determine a subsequent sampled state based on the modular energy function and the one or more design conditions. The final sampled state is a protein backbone, e.g., defined by three-dimensional coordinates of residue heavy atoms in the protein chain.

In one or more embodiments, the analytics system 420 may generate a full amino acid sequence configured to structurally create the protein backbone. In one or more embodiments, the diffusion model may be trained to further output the full amino acid sequence. In other embodiments, the analytics system 420 deploys a sequence generation model to determine the full amino acid sequence. The sequence generation model inputs the protein backbone and outputs the full amino acid sequence.

Prior to deployment of the diffusion model, the analytics system 420 may train the diffusion model. The analytics system 420 retrieves protein backbones for use as training samples, e.g., from a database. With each protein backbone, the analytics system transforms an initial state of the protein backbone into a noised state by injecting noise. The amount of noise injected is based on random sampling of a time step on a time continuum. At training time, the analytics system 420 applies the diffusion model to the noised states of the training samples to predict a denoised state from the noised state. The denoised state is predicted based on a gradient of an energy function as applied to the noised state. The analytics system 420 may determine a loss for each training sample based on the initial state and the denoised state. The analytics system 420 trains the diffusion model, e.g., by adjusting parameters (also referred to as weights) of the diffusion model, to minimize the losses. In one or more embodiments, the analytics system 420 leverages flexible sampling via a modified sampling operation. The analytics system 420 may modify the sampling operation with one or more sampling parameters and their associated values.

In one or more embodiments, the analytics system 420 includes the diffusion model 455, a conditioner module 460, a training module 465, and a sampling module 470, a sequence generation model 475, a protein folding model 480, a conditioner database 485, and a protein database 490. In other embodiments, the analytics system 420 may have additional, fewer, or different components than those listed in FIG. 2.

The diffusion model 455 is configured to transform one state of a protein backbone into another state of the protein backbone through removal of noise. The diffusion model 455 is a computation, machine-learning generative model.

The diffusion model 455 simulates the forward and reverse diffusion of a protein backbone on a time continuum, i.e., where $t \in [0, 4]$. The denoised state is at time step $t=0$, whereas time step $t=1$ represents complete diffusion and thereby loss of any signal. When training the diffusion model 455, the diffusion model 455 learns to predict the reverse flow of time, from a noised state (at some time step in the time continuum) to the denoised state at time step $t=0$. At run-time, the diffusion model 455 is configured to predict small steps of reverse diffusion that is guided by a sampling algorithm employed by the sampling module 465. The diffusion model 455 inputs one state and outputs another state based on the input state and an energy function. In one or more embodiments, the energy function is a modular energy function defined by a diffusion energy component and one or more conditioner energy components. The diffusion energy component is a baseline energy component, whereas the conditioner energy components further modify the energy function to satisfy the one or more design conditions. Further details relating to the diffusion model 455 are described below in conjunction with FIGS. 5 & 6.

The conditioner module 460 conditions deployment of the diffusion model 455 based on a set of one or more design conditions. Design conditions are target characteristics of a target protein. The design conditions may include one or more restraints and one or more constraints. The restraints are soft conditions that bias the diffusion model to achieve a target characteristic. The constraints are hard conditions that limit the multidimensional protein space to ensure target protein wholly satisfies the constraints. Example design conditions include, but are not limited to, a symmetry constraint, a substructure infilling restraint, a shape constraint, a distance constraint, a substructure root mean squared deviation (RMSD) constraint, a text caption restraint, a sequence constraint, a domain classifier constraint, a secondary structure constraint, etc. The symmetry constraint specifies a certain symmetry of the target protein. The substructure infilling restraint biases towards particular substructures. The shape constraint specifies a particular shape of the target protein. The distance constraint specifies a particular distance between at least two residues. The substructure RMSD constraint specifies a structural motif to have a low RMSD. The text caption restraint biases towards a text input including one or more design conditions. The sequence constraint specifies the target protein to include a particular amino acid sequence. The secondary structure constraint specifies a particular secondary structure to be present in the target protein. In one or more embodiments, the conditioner module 460 applies a natural language processing (NLP) model to parse a text query into the one or more design conditions. The NLP model may be machine-learning model.

In one or more embodiments, the conditioner module 460 generates the modular energy function based on the set of one or more design conditions. The conditioner module 460 may generate the modular energy function by selecting a baseline conditioner energy component for each design condition. The conditioner module 460 may further modify the conditioner energy component based on the design condition. For example, the conditioner energy component for the distance constraint may include a variable for the distance value specified. Accordingly, the conditioner module 460 fills in the variable of the baseline conditioner energy component with the specified distance value. In other examples, the symmetry constraint design condition may include different conditioner energy components for each type of possible symmetry. Further details relating to different design conditions are described below in the subsection entitled "Conditioner Examples."

The sampling module 465 implements a flexible sampling algorithm to traverse the multidimensional protein space with the diffusion model 455 to generate a de novo protein. Initially, the sampling module 465 may determine the initial sampled state. The initial sampled state may be a random state in the multidimensional protein space. The sampling module 465 iteratively inputs one sampled state into the diffusion model 455 to generate another sampled state based on the modular energy function as applied to the first sampled stated. The sampling module 465 iterates over a plurality of sampling steps. In one or more embodiments, the number of sampling steps is based on a time increment. For example, if the sampling module initializes a random state at $t=0.850$ on the time continuum that ranges $t \in [0, 1]$, with $t_0=0$ as the time step of the initial state, then the number of sampling steps is 850 with a time increment $\Delta t=0.001$. The final sampled state where $t=0$ is the de novo protein backbone.

In some embodiments, the sampling module 465 may leverage a constrained space defined by the set of one or more design conditions. The sampling module 465 transforms an input sampled state in unconstrained space into constrained space based on the one or more design conditions. The sampling module 465 may denoise the input state in the constrained space. The sampling module 465 may transform the denoised input state from the constrained space back into the unconstrained space. Then the sampling module 465 may apply the gradient of the diffusion model's modular energy function to the input sampled state (e.g., after denoising in the constrained space, and transformed back into the unconstrained space) to determine an output sampled state.

In some embodiments, the sampling module 465 modifies the sampling operation according to one or more sampling parameters and their associated values. Example sampling parameters includes a momentum, a mass, a friction, an equilibration, and an inverse temperature. The sampling parameters and associated values may be input by a user. During the diffusion process, the sampling module 465 may further tune the sampling operation to improve navigation of the energy landscape.

The training module 470 trains the diffusion model 455. The training module 470 may train the diffusion model to predict a reverse-time diffusion process of protein backbones. The training module 470 may obtain a set of known protein backbones to use as training samples for training the diffusion model 455. The known protein backbones may be accessed from the third-party database 430. For each known protein backbone's initial state, the training module 470 may inject an amount of noise based on a randomly sampled time step on the time continuum. For example, the time continuum ranges $t \in [0, 4]$, with $t_0=0$ as the time step of the initial state and $t_n$ is the randomly selected time step on the time continuum. At $t=1$, all signal is lost, and the protein backbone is completely noised. The greater the time step, the more noise is injected into the training sample. The training module 470 trains the diffusion model 455 to predict the initial state from the noised state. To accomplish the training, the training module 470 applies the diffusion model 455 to the noised state to predict the denoised state. The training module 470 calculates, for each training sample, a loss between the initial state and the predicted denoised state. The training module 470 tunes the diffusion model 455, i.e., by adjusting parameters of the diffusion model 455, to minimize the losses of the training samples. As the training module 470 trains the diffusion model 455 by directly predicting the initial state, the training scales $O$ (N). Further details related to training of the diffusion model 455 are described in conjunction with FIG. 5.

The sequence generation model 475 generates a full amino acid sequence for a de novo protein backbone. The sampling module 465 provides the de novo protein backbone, i.e., which describes the x3D coordinates of the heavy atoms in each amino acid sequence. The sequence generation model 475 inputs the de novo protein backbone to output the full amino acid sequence that structurally creates the de novo protein backbone. In one or more embodiments, the sequence generation model 475 may further output the DNA sequence for coding the protein. The sequence generation model 475 may be trained as a machine-learning model based on known protein backbones with corresponding known amino acid sequences. In some embodiments, the training module 470 trains the sequence generation model 475 by applying the sequence generation model 475 to a known protein backbone to predict a full amino acid sequence for the known protein backbone. The training module 470 may calculate a loss for each known protein backbone based on a comparison (e.g., a difference) between the predicted full amino acid sequence and the corresponding known amino acid sequence.

The protein folding model 480 validates the full amino acid sequence generated by the sequence generation model 475. The protein folding model 480 inputs an amino acid sequence and determines a protein backbone based on the input amino acid sequence. The protein folding model 480 may be applied to the full amino acid sequence, e.g., generated by the sequence generation model 475, to validate whether the full amino acid sequence successfully folds into the de novo protein backbone. The protein folding model 480 may be retrieved from the third-party database 430. The protein folding model 480 may also be trained by the training module 470, e.g., with known protein backbones and corresponding known amino acid sequences.

The conditioner database 485 stores the one or more baseline conditioner energy components for use by the conditioner module 460. As described above, each type of design condition may be associated with one or more baseline conditioner energy components. The baseline conditioner energy component may include one or more variables to be filled in based on the design condition input by the client device 410. For example, with the symmetry constraint, the conditioner database 485 may store a conditioner energy component for each symmetry.

The protein database 490 stores information on proteins. For example, the protein database 490 stores known protein backbones and corresponding known amino acid sequences, e.g., for training of the various models. The protein database 490 may further store proteins generated by other modules of the analytics system 420. For example, the protein database 490 may store the generated protein backbones and/or the corresponding full amino acid sequences. The protein database 490 may further store results of validation experiments. For example, the analytics system 420 may provide a full amino acid sequence for a de novo protein design to the protein manufacturing system 440 to validate the synthetic protein. The protein manufacturing system 440 may manufacture the synthetic protein and conduct one or more validation experiments to assess characteristics of the manufactured synthetic protein.

The third-party database 430 is an online database that stores data, e.g., that may be retrieved and used by the analytics system 420. In one or more embodiments, the third-party database 430 stores data on past protein designs. Each protein design may be described by a nucleic acid sequence coded for expression of the protein, an amino acid sequence of the protein (and variants thereof), information on protein folding structure, protein function, chemical properties, physical properties, thermodynamic properties, etc.

The protein manufacturing system 440 is a platform for manufacturing protein. In some embodiments, the protein manufacturing system 440 may be a human-operated laboratory environment. In other embodiments, the protein manufacturing system 440 may be an automated platform with one or more devices for manufacturing protein. For example, the protein manufacturing system 440 may include a DNA synthesis device for manufacturing DNA molecules for coding a target protein. The DNA synthesis device may implement chemical synthesis to create the DNA molecules. Chemical synthesis is a solid-phase phosphoramidite chemical process. In chemical synthesis, the desired DNA sequence is built step-by-step by adding one nucleotide at a time. The process occurs on a solid support, usually a controlled pore glass bead, where the first nucleotide is attached. The synthesis proceeds using a series of reactions to add each subsequent nucleotide successively. This method can produce DNA molecules, e.g., up to 200 base pairs long. These synthesized DNA molecules can be assembled into larger constructs. The protein manufacturing system 440 may also include another protein synthesis device for protein expression with the synthetically generated DNA molecules coded for expression of the target protein. The protein synthesis device may be configured to transfect a cell line with the synthetically generated DNA molecules. Example cell lines include bacteria, yeast, and mammalian cells. The choice of host cell system depends on factors such as scalability, cost, and compatibility with the protein's structure and function. The transfected cell lines are maintained to produce the protein through the cell's natural functions. Following protein expression, the protein manufacturing system 440 may perform protein extraction and purification to yield a high-quality and functional protein product. Common purification methods include affinity chromatography, ion exchange chromatography, size exclusion chromatography, and precipitation. The end result is the extracted and purified target protein.

In some embodiments, the protein manufacturing system 440 may also perform one or more wet lab analyses on the protein manufactured. Wet lab analyses aim to characterize or to validate the manufactured protein. For example, the protein manufacturing system 440 may sequence the manufactured protein to determine whether the manufactured protein matches to the intended target protein. In other examples, the protein manufacturing system 440 may characterize the structure of the manufactured protein, e.g., through x-ray crystallography. The protein manufacturing system 440 may further run experiments with the manufactured protein while measuring characteristics, e.g., denaturing the manufacture protein to determine refolding structure, etc.

The client device 410, the analytics system 420, the third-party database 430, and the protein manufacturing system 440 can communicate with each other via the network 450. The network 450 is a collection of computing devices that communicate via wired or wireless connections. The network 450 may include one or more local area networks (LANs) or one or more wide area networks (WANs). The network 450, as referred to herein, is an inclusive term that may refer to any or all of standard layers used to describe a physical or virtual network, such as the physical layer, the data link layer, the network layer, the transport layer, the session layer, the presentation layer, and the application layer. The network 450 may include physical media for communicating data from one computing device to another computing device, such as multiprotocol label switching (MPLS) lines, fiber optic cables, cellular connections (e.g., x3G, 4G, or 5G spectra), or satellites. The network 450 also may use networking protocols, such as TCP/IP, HTTP, SSH, SMS, or FTP, to transmit data between computing devices. In some embodiments, the network 450 may include Bluetooth or near-field communication (NFC) technologies or protocols for local communications between computing devices. The network 450 may transmit encrypted or unencrypted data.

Diffusion Model Training & Deployment for de Novo Protein Design

Figure 5:
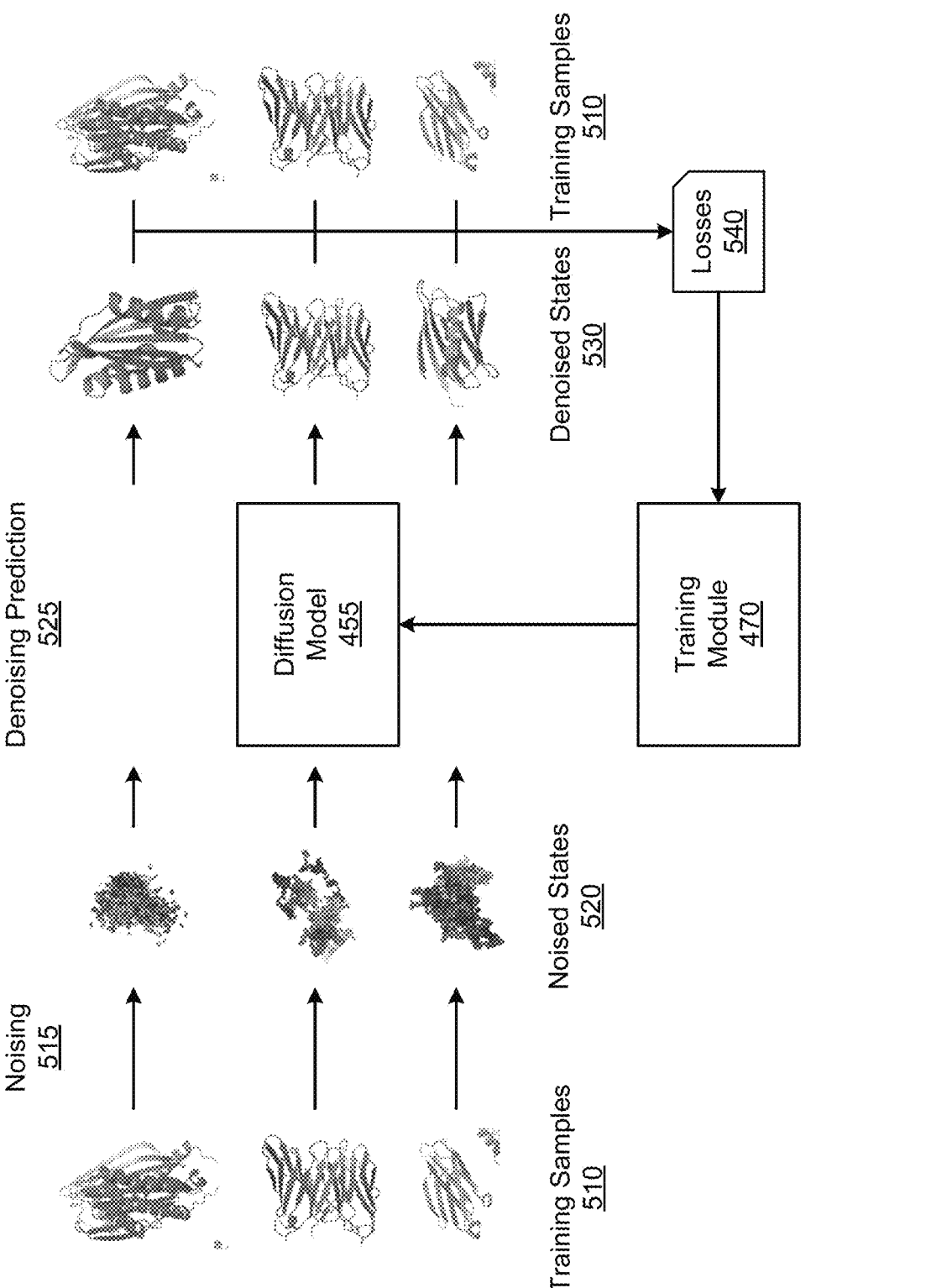
FIG. 5 illustrates a training process of the diffusion model, according to one or more embodiments.

FIG. 5 illustrates a training process of the diffusion model 455, according to one or more embodiments. The training process may be performed by the analytics system 420, or more specifically the training module 470. The training process is representatively illustrated as the use of three training samples 510, but any number of training samples may be used in the training process. Each reference numeral may be referenced in the singular when referring to individual units or in the plural when referring to the whole set.

To train the diffusion model 455, the analytics system 420 utilizes training samples 510. The training samples 510 may be known protein backbones, e.g., as retrieved from the third-party database 430. The analytics system 420 injects some noise into each known protein backbone to generate a noised state 520 for each known protein backbone. As noted above, the amount of noise may be based on the randomly sampled time step on the time continuum.

The analytics system 420 may filter the training samples 510 to refine the training of the diffusion model 455. For example, the analytics system 420 may deduplicate training samples 510 that are similar. To assess whether two training samples 510 are similar, the analytics system 420 may calculate a distance between the protein backbones of the two training samples 510. The distance may be calculated as the difference in protein folding structure, and may be as granular as calculating differences between relative positions of heavy atoms in the backbones. If the distance is below a threshold distance, then the analytics system 420 may retain one training sample, whilst excluding the second training sample as redundant. The analytics system 420 may also focus training of the diffusion model 455 to certain types of proteins, e.g., antibodies. In some embodiments, the analytics system 420 may apply a different threshold distance between different types of proteins to bias training of the diffusion model 455 towards particular types of proteins.

In some embodiments, the analytics system 420 may generate multiple training samples 510 from one known protein backbone. For example, the analytics system 420 may generate a first training sample 510 by injecting a first amount of noise to the known protein backbone and may generate a second training sample 510 by injecting a different amount of noise to the known protein backbone. The analytics system 420 may also generate synthetic protein backbones by introducing one or more modifications to the known protein backbones.

The analytics system 420 applies the diffusion model 455 to each noised state 520 to predict a denoised state 530 for each training sample 510. The analytics system 420 calculates a loss 540 for each training sample 510. The loss 540 may be calculated as a difference between the denoised states 530 and the initial states of the training samples 510. The training module 475, thereafter, trains the diffusion model 455 by adjusting parameters of the diffusion model 455 to minimize the losses 540.

Figure 6:
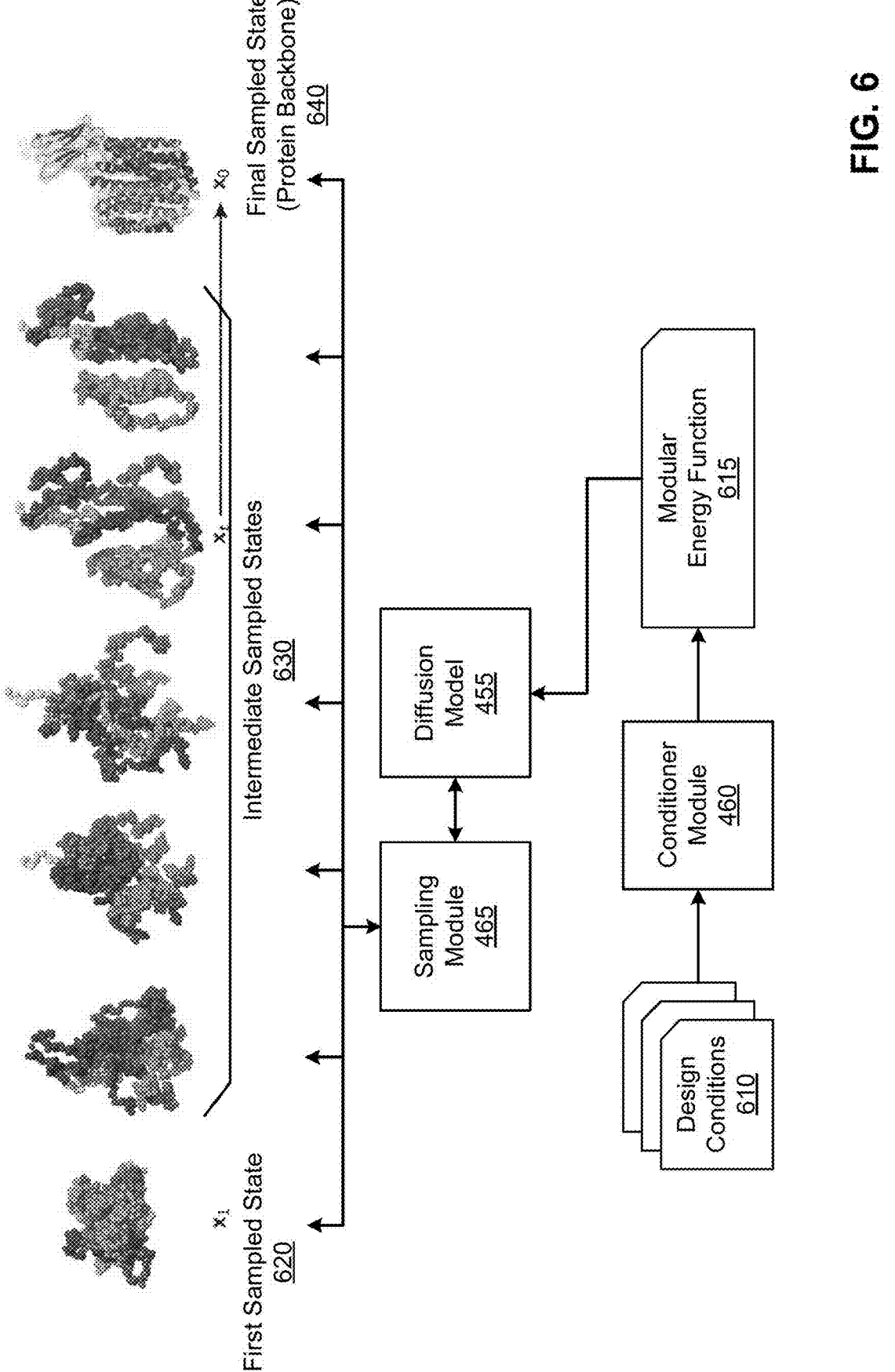
FIG. 6 illustrates deployment of the diffusion model to generate a protein backbone based on a set of one or more design conditions, according to one or more embodiments.

FIG. 6 illustrates deployment of the diffusion model 455 to generate a protein backbone based on a set of one or more design conditions, according to one or more embodiments. The deployment of the diffusion model 455 may be performed by the analytics system 620. The training process is representatively illustrated as performing seven sampling steps, but any number of sampling steps may be used in the deployment process. Each reference numeral may be referenced in the singular when referring to individual units or in the plural when referring to the whole set.

The analytics system 620 receives design conditions 610, e.g., from the client device 610. The design conditions 610 may include one or more restraints, one or more constraints, or some combination thereof. The design conditions 610 specify target characteristics of the protein to be generated. The conditioner module 460 generates a modular energy function 615 based on the design conditions 610. The modular energy function 615 includes a diffusion energy component and one or more conditioner energy components corresponding to the design conditions 610. The modular energy function 615 is utilized by the diffusion model 455 during the sampling process.

The sampling module 465 initializes the sampling process with a first sampled state 620. The first sampled state 620 may be a random state in the multidimensional protein space. In some embodiments, the client device 610 may provide an initial sampled state to serve as a launch point. In a first sampling step, the sampling module 465 inputs the first sampled state 620 into the diffusion model 455 to output a second sampled state (not shown in FIG. 6) based on a gradient of the modular energy function 615. In one or more embodiments, the sampling module 465 may also transform the first sampled state 620 from unconstrained space into constrained space based on the one or more design conditions (e.g., the constraints). The diffusion model 455 denoises in the constrained space. Then the sampling module 465 transforms back into unconstrained space, where the sampling module 465 applies the diffusion model 455 to output the second sampled state. In subsequent sampling steps, the sampling module 465 iteratively inputs a sampled state to output a subsequent sampled state making up the intermediate sampled states 630, e.g., with an incremented reverse time step, trending towards t=0. The final sampled state 640 at t=0 is the de novo protein backbone.

During the diffusion process, the sampling module 465 may leverage a modified sampling operation (e.g., as described above in FIG. 1 and corresponding description) to traverse the protein space. Moreover, the sampling module 465 may perform sampling processes (in parallel or in series). The analytics system 420 may assess each sampling process (and the modified sampling operation) by measuring and comparing characteristics of the final sampled states achieved through the sampling processes. For example, the analytics system 420 may measure the diversity in protein designs. The analytics system 420 may provide the measured characteristics to a user, e.g., via a client device, to inform the user on how the sampling parameters affect the sampling process. For example, the analytics system 420 may indicate that lowering the inverse temperature may increase diversity of the resulting outputs, but with the tradeoff of not fully exploiting high-likelihood regions of the energy landscape. Or, as another example, the analytics system 420 may indicate that increasing the momentum may increase speed of convergence by dampening oscillations with the tradeoff of potentially overshooting optima and creating its own oscillations.

Methods

FIG. 7 is a method flowchart of sampling 700 with a flexible sampling operation, according to one or more embodiments. The sampling 700 is described as performed by a system (e.g., the optimization system 100 of FIG. 1, or the analytics system 420 of FIG. 4). In other embodiments, any step of the sampling 700 may be performed by another computing system or device in conjunction with the system. In other embodiments, the sampling 700 may include additional, fewer, or different steps than those listed herein (as will also be described throughout FIG. 7 description).

The system receives 710 user input to tailor sampling of a complex function. The user input includes a permutation of one or more sampling parameters (selected from a list of available sampling parameters) and the parameter values for the selected sampling parameters. The system may receive the user input via a user interface, e.g., presented on a display on a client device or the system. The user interface may provide user-interactable elements for inputting the user input. For example, the user-interactable elements may include buttons for selecting from the available sampling parameters. In other examples, the user-interactable elements may include one or more sliders, wherein a slider dictates a parameter value for a sampling parameter.

The system modifies 720 a baseline sampling operation based on the user input. Modifying may include incorporating the selected sampling parameters and their associated values, i.e., indicated by the user input. Unselected sampling parameters are excluded from the modification step.

The system performs 730 sampling of the complex function with the modified sampling operation to find a set of one or more candidate optima of the complex function. The system may perform a number of sampling processes in parallel using the same modified complex function but from different initial candidate solutions. The system may perform a sampling process until a stop condition is met, e.g., upon completion of a total number of sampling steps, upon marginal change or improvement in the candidate solution, etc. In some embodiments, the system may perform sampling processes in parallel with different modified sampling operations. In additional embodiments, the system may perform a set of sampling processes for each of a set of modified sampling operations. Each sampling process can yield a plurality of candidate solutions, wherein the terminal candidate solution may be the identified optimum by the sampling process.

The system can return the optima, e.g., to a user of the system. In some embodiments, the system may visualize the sampling process(es) providing real-time feedback to the user, e.g., of how each modified sampling operation performs compared to others. The returned optima may include generative images in a context of image generation via a diffusion model. The returned optima may include protein folding structure in a context of protein structure solving. The returned optima may include synthetic protein backbones in a context of de novo protein design via a diffusion model. The returned optima may include a distribution schema of available resources to optimize for one or more objectives of a real-world system. The returned optima may include one or more actions for a real-world system to perform in order to optimize for one or more objectives.

In one or more embodiments, the system evaluates 740 the one or more candidate optima against one or more metrics. The system may evaluate diversity of the candidate optima. For example, with one modified sampling operation, the system can evaluate diversity in the optima identified by different sampling processes performed using that one modified sampling operation. In another example, the system can evaluate the diversity of the set of optima identified according to each of a plurality of modified sampling operations. In another example, the system may evaluate speed of convergence, oscillations by the sampling process, quality of optima identified, exploration of the search space, etc. The system may score each permutation of sampling parameters and associated values based on the evaluated metrics. The score generally reflects efficiency of the permutation in exploring and/or exploiting the complex function space, given the limited computation budget.

In one or more embodiments, the system tunes 750 the sampling operation by adjusting selection of sampling parameters and/or parameter values. In tuning the sampling operation, the system may evaluate empirical data of past sampling processes. For example, the system may learn that the modified sampling operation according to one permutation yields a lot of noisy results, then the system may adjust one or more parameter values to improve the sampling of the complex function space. For example, the system can toggle a value for the inverse temperature.

In one or more embodiments, the system performs 760 subsequent sampling of the complex function with the tuned sampling operation to find a subsequent set of one or more candidate optima of the complex function. The system can, as described in step 730, perform a plurality of sampling processes with the tuned sampling operation in parallel, yielding a plurality of optima from the plurality of sampling processes. The optima may be returned to the user, e.g., evaluated, ranked, and selected.

In one or more embodiments, the system can iteratively tune the sampling operation. The system may re-evaluate the optima identified with the tuned sampling operation. The system may reassess whether further tuning is needed. If so, the system may determine how to further tune the sampling operation and proceed with additional tuning of the sampling operation. The system may perform subsequent sampling with the further tuned sampling operation.

In some embodiments, the system may perform the tuning during a sampling process. The system may assess the sampling's traversal of the complex function space during the sampling process. Based on one or more insights into the traversal, the system may automatically and adaptively tune the sampling operation.

In one or more embodiments, the system may apply a machine-learning model to learn which permutations might best traverse a complex function space. The system can learn such insights by training the machine-learning model based on empirical data, i.e., historical sampling processes performed with various permutations used in modifying the sampling operation. The learned insights may be used to provide visual indication of optimal ranges in a user interface for toggling the sample parameters.

FIG. 8 illustrates a flowchart describing training 800 of a diffusion model for protein design, according to one or more embodiments. The training 800 is described as performed by an analytics system (e.g., the analytics system 420 of FIG. 4). In other embodiments, any step of the training 800 may be performed by another computing device in conjunction with the analytic system. In other embodiments, the training 800 may include additional, fewer, or different steps than those listed herein (as will also be described throughout FIG. 8 description).

The analytics system accesses 810, from a protein database, a set of known protein backbones. The protein database may be a third-party database 130. The protein database stores information relating to known proteins. In some embodiments, the analytics system retrieves the amino acid sequences of the known proteins and generates a protein backbone based on a protein folding model. Each protein backbone describes three-dimensional coordinates of each heavy atom of each amino acid residue in the protein's peptide chain. In other embodiments, the protein backbone may further describe the three-dimensional coordinates of atoms on a sidechain of each amino acid residue.

The analytics system may filter 820 the set of protein backbones to achieve a training set of protein backbones for use in training the diffusion model. In one or more embodiments, filtering includes deduplication of similar protein backbones. To determine if two protein backbones are similar, the analytics system may determine a similarity score as a distance between the coordinates of the two protein backbones. If the similarity score is below a threshold, then the two protein backbones may be deemed sufficiently similar. Accordingly, the analytics system may remove one of the two similar protein backbones. In other embodiments, filtering may include obtaining a high percentage of protein backbones of one or more particular types of protein.

The analytics system generates 830 a noised state for each protein backbone by transforming an initial state of the protein backbone with noise. As the diffusion model learns a reverse-time diffusion process, the analytics system may generate the training samples by simulating forward-time diffusion. The amount of noise added to the initial state may be based on a randomly selected time step on the time continuum. The noise may be Gaussian noise. In some embodiments, the analytics system may generate multiple training samples from one known protein backbone by adding differing amounts of noise to the initial state, thereby generating two distinct noised states.

The analytics system applies 840 the diffusion model to the noised state of each protein backbone to predict a denoised state of the protein backbone. The analytics system applies the diffusion model to predict the initial time step associated with the initial state of the protein backbone. The diffusion model may predict the denoised state based on a gradient of an energy function as applied to the noised state.

The analytics system determines 850 a loss of each protein backbone as a difference between the denoised state and the initial state of the protein backbone. In one or more embodiments, the difference may be a L1 norm, a L2 norm, some other distance calculation, or some combination thereof.

The analytics system trains 860 the diffusion model as a neural network by adjusting one or more parameters of the diffusion model based on the losses. The analytics system may backpropagate through the diffusion model to adjust parameters to minimize the losses between the predicted denoised states and the initial states. In some embodiments, the analytics system may perform batch training of the diffusion model, which generally entails adjusting parameters of the diffusion model to minimizes losses for a batch of training samples. In other embodiments, the analytics system may perform iterative training over epochs. An epoch of training is an instance parameter adjustment from a complete pass of the training set through the diffusion model. The diffusion model may be structured with the architectures described in FIGS. 5 & 6.

The trained diffusion model may be stored in a database of the analytics system, and/or the trained diffusion model may transmitted to one or more other computing devices. When fully trained, the analytics system may deploy the diffusion model in conjunction with a sampling algorithm to generate a de novo protein design.

FIG. 9 illustrates a flowchart describing de novo protein generation 900 through deployment of a diffusion model, according to one or more embodiments. The de novo protein generation 900 is described as performed by an analytics system (e.g., the analytics system 420 of FIG. 4). In other embodiments, any step of the de novo protein generation 900 may be performed by another computing device in conjunction with the analytic system. In other embodiments, the de novo protein generation 900 may include additional, fewer, or different steps than those listed herein (as will also be described throughout FIG. 8 description).

The analytics system receives 910 a set of one or more design conditions that specify target characteristics of a synthetic protein. The set of one or more design conditions may be parsed from a text query by a client device. For example, the text query may be "design an antibody with C5 symmetry with Beta hairpin motifs." The analytics system may parse the text query, e.g., with a NLP model, to determine the one or more design conditions. Following the above example, the analytics system may determine a symmetry constraint of "C5 symmetry," a text caption restraint of "antibody," and a secondary structure constraint of "Beta hairpin motif."

Other types of design conditions may include, but are not limited to, a symmetry constraint, a substructure infilling restraint, a shape constraint, a distance constraint, a substructure root mean squared deviation (RMSD) constraint, a text caption restraint, a sequence constraint, a domain classifier constraint, a secondary structure constraint, etc.

The analytics system defines 920 a modular energy function as a composition of a diffusion energy component and one or more conditioner energy components. The diffusion energy component determines an energy value based on a sampled state of the synthetic protein and a time step of the sampled state. Each conditioner energy component determines an energy value based on the sample state of the synthetic protein and the target characteristic of each design condition. The conditioner energy components may be pulled together based on the set of design conditions received, e.g., from the client device. As such, one design query having one set of design conditions yields a different modular energy function compared to another design query having a distinct set of design conditions. In some embodiments, the conditioner energy components include one or more variables that are filled in based on the received design conditions.

The analytics system may rescale 930 the modular energy function based on a time-dependent temperature and/or a time-dependent Langevin dynamics equilibration rate. The time-dependent temperature enables an adjustable temperature throughout the sampling process, such that the sampling can bias towards high likelihood regions in the multidimension protein space. The time-dependent Langevin dynamics equilibration rate sets the equilibration rate of the Langevin dynamics per unit time. The equilibration rate effectively operates to promote exploration as a counterbalance to low-temperature as a driver of exploitation. The high-likelihood states exhibit increased rates of backbone hydrogen bonding that underlie secondary structure.

The analytics system applies 940 the diffusion model to generate a denoised protein backbone. To generate the denoised protein backbone, the analytics system iteratively samples the multidimensional space with the diffusion model, e.g., trained according to the training 800 in FIG. 8. The initialize the sampling, the analytics system may randomly sample a noised state in the multidimensional protein space.

In one sampling step: the analytics system transforms 950 the prior sample state from unconstrained space into constrained space based on the one or more design conditions. For example, if one design condition is an amino acid sequence constraint, then the analytics system constrains the sampled state to substitute some portion of the sampled state of the protein backbone to include the specified amino acid sequence. In the same sampling step: the analytics system denoises 960 the prior sampled state in the constrained space. The analytic system denoises by determining an amount of noise in the sampled state and removing that amount of noise. In the same sampling step: the analytics system samples 970 a subsequent sampled state in the unconstrained space by applying a gradient of the modular energy function to the denoised prior sampled sate in the constrained space. The subsequent sampled state is one subsequent incremented time step, i.e., towards $t \rightarrow 0$. The analytics system iteratively performs sampling over a plurality of discrete sampling steps to incrementally progress from the first sampled state to the final sampled state, being the denoised protein backbone.

In further embodiments, the analytics system applies a sequence generation model to the denoised protein backbone to determine a full amino acid sequence for the synthetic protein. The sequence generation model inputs the denoised protein backbone and determines an amino acid sequence that can fold to structurally create the denoised protein backbone. The sequence generation model may further output the sidechain sequences, completing the all-atom structure.

In additional embodiments, the analytics system may perform parallel sampling of the multidimensional protein space with different seed sampled states. The analytics system may use each seed sampled state to generate a diverse set of de novo protein designs that satisfy the set of one or more design conditions. The analytics system may provide the diverse set of de novo protein designs for experimental validation, e.g., of protein folding, of function, etc.

Additional Considerations

The foregoing description of the embodiments has been presented for the purpose of illustration; many modifications and variations are possible while remaining within the principles and teachings of the above description.

Any of the steps, operations, or processes described herein may be performed or implemented with one or more hardware or software modules, alone or in combination with other devices. In some embodiments, a software module is implemented with a computer program product comprising one or more computer-readable media storing computer program code or instructions, which can be executed by a computer processor for performing any or all of the steps, operations, or processes described. In some embodiments, a computer-readable medium comprises one or more computer-readable media that, individually or together, comprise instructions that, when executed by one or more processors, cause the one or more processors to perform, individually or together, the steps of the instructions stored on the one or more computer-readable media. Similarly, a processor may comprise one or more subprocessing units that, individually or together, perform the steps of instructions stored on a computer-readable medium.

Embodiments may also relate to a product that is produced by a computing process described herein. Such a product may store information resulting from a computing process, where the information is stored on a non-transitory, tangible computer-readable medium and may include any embodiment of a computer program product or other data combination described herein.

The description herein may describe processes and systems that use machine-learning models in the performance of their described functionalities. A "machine-learning model," as used herein, comprises one or more machine-learning models that perform the described functionality. Machine-learning models may be stored on one or more computer-readable media with a set of weights. These weights are parameters used by the machine-learning model to transform input data received by the model into output data. The weights may be generated through a training process, whereby the machine-learning model is trained based on a set of training examples and labels associated with the training examples. The training process may include: applying the machine-learning model to a training example, comparing an output of the machine-learning model to the label associated with the training example, and updating weights associated for the machine-learning model through a back-propagation process. The weights may be stored on one or more computer-readable media, and are used by a system when applying the machine-learning model to new data.

The language used in the specification has been principally selected for readability and instructional purposes, and it may not have been selected to narrow the inventive subject matter. It is therefore intended that the scope of the patent rights be limited not by this detailed description, but rather by any claims that issue on an application based hereon.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive "or" and not to an exclusive "or". For example, a condition "A or B" is satisfied by any one of the following: A is true (or present) and B is false (or not present); A is false (or not present) and B is true (or present); and both A and B are true (or present). Similarly, a condition "A, B, or C" is satisfied by any combination of A, B, and C being true (or present). As a not-limiting example, the condition "A, B, or C" is satisfied when A and B are true (or present) and C is false (or not present). Similarly, as another not-limiting example, the condition "A, B, or C" is satisfied when A is true (or present) and B and C are false (or not present).

What is claimed is:

1. A computer-implemented method comprising:
receiving, via a graphical user interface, a text prompt that specifies features of a synthetic image to be generated;
generating one or more embeddings for the text prompt in an embedding space;
receiving a set of one or more sampling parameters that tailor sampling, wherein the set of one or more sampling parameters includes a combination of a momentum sampling parameter, a mass sampling parameter, a friction sampling parameter, an equilibration sampling parameter, and an inverse temperature sampling parameter;
modifying a sampling operation based on the set of one or more sampling parameters to yield a first modified sampling operation;
applying a diffusion model to generate the synthetic image, wherein applying the diffusion model comprises, in each sampling step of a plurality of sampling steps:
denoising a prior sampled state of the synthetic image based on the one or more embeddings of the text prompt; and
sampling a subsequent sampled state from the denoised prior sampled state by applying the first modified sampling operation,
wherein a final sampled state is the synthetic image that satisfies the features of the text prompt; and
providing, via the graphical user interface, the synthetic image for presentation.

2. The computer-implemented method of claim 1, wherein the momentum sampling parameter accumulates sampling momentum of one or more prior sampled states, and wherein sampling the subsequent sampled state comprises sampling along the sampling momentum.

3. The computer-implemented method of claim 2, wherein the friction sampling parameter is a refreshment rate of the sampling momentum, and wherein sampling the subsequent sampled state comprises sampling along the sampling momentum dampened by the refreshment rate.

4. The computer-implemented method of claim 1, wherein the mass sampling parameter couples one or more degrees of freedom, and wherein sampling the subsequent sampled state comprises sampling with the one or more degrees of freedom coupled together.

5. The computer-implemented method of claim 1, wherein the equilibration sampling parameter injects equilibrium sampling into non-equilibrium sampling in the sampling operation for the diffusion model, and wherein sampling the subsequent sampled state comprises sampling in a combination of the equilibrium sampling and the non-equilibrium sampling.

6. The computer-implemented method of claim 1, wherein the inverse temperature sampling parameter guides sampling towards exploitation of high-likelihood states, and wherein sampling the subsequent sampled state comprises sampling from a high-likelihood region.

7. The computer-implemented method of claim 1, wherein applying the diffusion model comprises, in between two sampling steps:
tuning the first modified sampling operation based on the prior sampled states by adjusting parameter values of one or more sampling parameters, wherein remaining sampling steps are performed with the tuned first modified sampling operation.

8. The computer-implemented method of claim 1, further comprising:
generating the graphical user interface for inputting the text prompt and the set of one or more sampling parameters and corresponding parameter values; and
presenting the graphical user interface to a user.

9. The computer-implemented method of claim 8, wherein generating the graphical user interface comprises:
generating the graphical user interface to include one or more sliders, wherein a position of each slider along a continuum indicates a parameter value for a corresponding sampling parameter.

10. The computer-implemented method of claim 9, wherein generating the graphical user interface comprises:

generating the graphical user interface to include an indication for each slider of a recommended range of parameter values for the corresponding sampling parameter.

11. The computer-implemented method of claim 8, wherein generating the graphical user interface comprises:

generating the graphical user interface to include a visualization of each sampled state in determining the synthetic image.

12. The computer-implemented method of claim 1, further comprising:

initializing a first seed state and a second seed state that is different than the first seed state;

wherein applying the diffusion model comprises applying the diffusion model to the first seed state to determine a first synthetic image and applying the diffusion model to the second seed state to determine a second synthetic image.

13. The computer-implemented method of claim 12, further comprising:

receiving a second set of one or more sampling parameters;

modifying the sampling operation to a second modified sampling operation based on the second set of sampling parameters; and wherein applying the diffusion model comprises applying the first modified sampling operation to the first seed state and applying the second modified sampling operation to the second seed state.

14. The computer-implemented method of claim 1, further comprising:

receiving a second set of one or more design conditions that specify one or more modifications to the synthetic image;

applying the diffusion model to modify the synthetic image to satisfy the one or more modifications.

15. A non-transitory computer-readable storage medium storing instructions that, when executed by a computer processor, cause the computer processor to:

receive, via a graphical user interface, a text prompt that specifies features of a synthetic image to be generated;

generate one or more embeddings for the text prompt in an embedding space;

receive a set of one or more sampling parameters that tailor sampling, wherein the set of one or more sampling parameters includes a combination of a momentum sampling parameter, a mass sampling parameter, a friction sampling parameter, an equilibration sampling parameter, and an inverse temperature sampling parameter;

modify a sampling operation based on the set of one or more sampling parameters to yield a first modified sampling operation;

apply a diffusion model to generate the synthetic image, wherein to apply the diffusion model comprises, in each sampling step of a plurality of sampling steps, to:

denoise a prior sampled state of the synthetic image based on the one or more embeddings of the text prompt; and sample a subsequent sampled state from the denoised prior sampled state by applying the first modified sampling operation, wherein a final sampled state is the synthetic image that satisfies the features of the text prompt; and provide, via the graphical user interface, the synthetic image for presentation.

16. A computer-implemented method comprising:

receiving, via a graphical user interface, a text prompt that specifies features of a structured data object to be generated;

generating one or more embeddings for the text prompt in an embedding space;

receiving a set of one or more sampling parameters that tailor sampling, wherein the set of one or more sampling parameters includes a combination of a momentum sampling parameter, a mass sampling parameter, a friction sampling parameter, an equilibration sampling parameter, and an inverse temperature sampling parameter;

modifying a sampling operation based on the set of one or more sampling parameters to yield a first modified sampling operation;

applying a diffusion model to generate the structured data object, wherein applying the diffusion model comprises, in each sampling step of a plurality of sampling steps:

denoising a prior sampled state of the structured data object based on the one or more embeddings of the text prompt; and sampling a subsequent sampled state from the denoised prior sampled state by applying the first modified sampling operation, wherein a final sampled state is the structured data object that satisfies the features of the text prompt;

rendering a visual representation of the structured data object; and providing, via the graphical user interface, the visual representation for presentation.

* * * * *